(12) United States Patent
Pajerski

(10) Patent No.: US 9,567,311 B2
(45) Date of Patent: Feb. 14, 2017

(54) WATER DISPERSIBLE, SELF-CROSSLINKABLE PREPOLYMER COMPOSITION

(71) Applicant: LUBRIZOL ADVANCED MATERIALS, INC., Cleveland, OH (US)

(72) Inventor: Anthony D. Pajerski, Broadview Heights, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 14/374,360

(22) PCT Filed: Jan. 23, 2013

(86) PCT No.: PCT/US2013/022670
§ 371 (c)(1),
(2) Date: Jul. 24, 2014

(87) PCT Pub. No.: WO2013/112530
PCT Pub. Date: Aug. 1, 2013

(65) Prior Publication Data
US 2014/0378607 A1  Dec. 25, 2014

Related U.S. Application Data

(60) Provisional application No. 61/590,847, filed on Jan. 26, 2012.

(51) Int. Cl.
| | | |
|---|---|---|
| C08G 59/14 | (2006.01) | |
| C08G 59/18 | (2006.01) | |
| C07D 303/42 | (2006.01) | |
| C08G 59/16 | (2006.01) | |
| C09D 133/06 | (2006.01) | |
| C09D 191/00 | (2006.01) | |

(52) U.S. Cl.
CPC ......... *C07D 303/42* (2013.01); *C08G 59/1461* (2013.01); *C08G 59/186* (2013.01); *C09D 133/068* (2013.01); *C09D 191/00* (2013.01); *C08L 2201/54* (2013.01); *C08L 2312/00* (2013.01)

(58) Field of Classification Search
CPC .................. C08G 59/1461; C08G 59/186
See application file for complete search history.

(56) References Cited

U.S. PATENT DOCUMENTS

| | | |
|---|---|---|
| 6,682,673 B1 | 1/2004 | Skwiercz et al. |
| 2008/0027168 A1 | 1/2008 | Pajerski |
| 2010/0330375 A1 | 12/2010 | Pajerski |

*Primary Examiner* — Vickey Nerangis
(74) *Attorney, Agent, or Firm* — Samuel B. Laferty, Esq.; Teresan W. Gilbert, Esq.

(57) ABSTRACT

The present invention provides an economical route to environmentally friendly polymeric coatings with a high content of raw materials from renewable resources. These polymeric coatings offer performance characteristics that are competitive with conventional coating systems. The unique polymers on which this invention is based are copolymers of triglyceride oils, such as soybean oil, linseed oil, or another natural oil, with a vinyl compound, such as an acrylate or methacrylate, or a vinyl aromatic monomer. The present invention more specifically discloses a water dispersible, self-crosslinkable prepolymer composition which is comprised of a triglyceride oil having appended thereto (1) hydroxyl groups, (2) epoxy groups, (3) moieties which contain at least one aldehyde group or at least one ketone group, and (4) moieties which contain at least one vinyl and/or substituted vinyl group. In one embodiment of this invention the moiety which contains at least one vinyl group is derived from maleic anhydride.

10 Claims, 2 Drawing Sheets

ESO-LA-MAA Prepolymer

WATER DISPERSIBLE, SELF-CROSSLINKABLE PREPOLYMER COMPOSITION

FIELD OF THE INVENTION

Prepolymers are disclosed that are free-radically co-polymerizable with other monomers. They can form polymers that are self-crosslinkable. Self-crosslinking can be achieved via a reaction sequence where a hydrazine containing moiety is added that can chemically react and bond to a carbon atom of a carbonyl (aldehyde or ketone type) attached to the prepolymer. The prepolymer can be made water dispersible by chemically bonding an anhydride of a di or polycarboxylic acid molecule via an ester linkage with pendant hydroxyl groups on the prepolymer.

BACKGROUND OF THE INVENTION

Waterborne dispersions are utilized in the coatings industry to provide substrates with aesthetic beauty, solvent and chemical resistance, mar and scuff resistance, and abrasion resistance. Such waterborne dispersions are commonly used for coating wood, masonry, plastic, textile, and metal products and can also be used in ink jet ink compositions. In recent years, waterborne dispersions have come into favor from an environmental standpoint as replacements for oil based coating compositions because they can be formulated with a low level of volatile organic compounds (VOCs) and are preferably free of volatile organic compounds.

The current trends in performance coatings are directed to environmentally friendly polymer types that contain a high content of raw materials based on renewable resources which can form coalesced films with low or reduced emissions of volatile organic compounds. Coatings of this type, accordingly, have reduced environmental impact. However, today waterborne polymers that offer reduced emissions of volatile organic compounds during film formation are typically based on petroleum derived raw materials or lack the performance needed in certain applications, such as wood flooring. This is particularly true in the case of one component self-crosslinking compositions which are more user friendly due to reduced toxicity concerns and more environmentally friendly due to less waste generated as compared to more conventional two component systems.

U.S. Pat. No. 4,066,591 and U.S. Pat. No. 4,147,679 disclose the preparation of waterborne polyurethane dispersions which contain unsaturated functional groups capable of undergoing auto-oxidative crosslinking.

U.S. Pat. No. 4,598,121 discloses a method for preparing an aqueous polyurethane dispersion, comprising (a) preparing a prepolymer with free NCO groups by reacting an aliphatic or cycloaliphatic polyisocyanate with a polyol, and an anionic compound; (b) dispersing said prepolymer in water; (c) reacting said water-dispersed prepolymer with a diamino hydrazide as a chain lengthening agent; and (d) reacting the prepolymer of step (e) in said dispersion with formaldehyde to effect crosslinking.

U.S. Pat. No. 4,983,662 discloses an aqueous self cross-linkable coating composition comprising an aqueous dispersion of at least one polyurethane and having hydrazine (or hydrazone) functional groups and carbonyl functional groups, disposed therein, to provide a self crosslinking reaction in which the polyurethane polymer takes part via azomethine formation during and/or after film formation.

U.S. Pat. No. 5,141,983 discloses a ketone-hydrazide crosslinking technology where the ketone, or carbonyl group resides on an acrylic polymer and a polyurethane polymer contains hydrazide functional groups. The composition is obtained by polymerizing the acrylic monomers in the presence of an aqueous polyurethane dispersion.

U.S. Pat. No. 5,571,861 and U.S. Pat. No. 5,623,016 disclose an aqueous, self-crosslinking polymer dispersion binder(s) comprising polyhydrazides and carbonyl-containing polyurethane-vinyl hybrid polymers and also, if desired, conventional additives are useful in base coatings, aqueous coatings, adhesives and printing inks.

U.S. Pat. No. 6,239,209 discloses waterborne urethane-acrylic compositions which are auto-oxidatively crosslinkable. In one embodiment, the composition also contains ketone hydrazide type self-crosslinking where the ketone/carbonyl is introduced via the acrylic and the hydrazide functionality is contained on the polyurethane along with the unsaturated oxidatively curable functional groups.

U.S. Pat. No. 6,576,702 discloses waterborne polyurethane dispersions are prepared by reacting (1) at least one polyisocyanate; (2) at least one active hydrogen containing compound, such as a polyol or a polyamide; and (3) preferably also at least one water-dispersibility enhancing compound having water-dispersion enhancing groups, in order to form an isocyanate terminated prepolymer. The prepolymer subsequently is (1) optionally neutralized by reaction with at least one neutralizing agent, (2) dispersed in water, and then (3) chain extended by reaction with at least one of water, inorganic or organic polyamine having an average of about 2 or more primary and/or secondary amine groups, or combinations thereof. At least one plasticizer is introduced into the reaction mixture at any time during prepolymer formation or before the prepolymer is dispersed in water. The plasticizer substantially or completely replaces other organic diluents or solvents. Various types of plasticizers may be employed, including reactive plasticizers.

United States Patent Application Publication No. 2010/0330375 discloses aqueous polyurethane dispersions that are made from urethane prepolymers comprising one or more polyhydroxy compounds from ketone functional molecules derived from an epoxidized natural oil. Addition of a hydrazine functional moiety to the prepolymer dispersion can further provide a crosslinking mechanism resulting in the formation of azomethine linkages in the resulting polyurethane during drying. When the ketone functional molecule is derived from levulinic acid and epoxidized vegetable oil, the resulting urethane dispersion can also be converted into a hybrid polyurethane-vinyl dispersion by adding and polymerizing one or more vinyl monomers in the polyurethane prepolymer or polyurethane dispersion. United States Patent Application Publication No. 2010/0330375, more specifically, reveals an aqueous polyurethane dispersion comprising at least one polyol obtained from the reaction of an epoxidized natural oil with an organic acid, wherein the polyol is reacted with a polyisocyanates to form a portion of the polyurethane. The novel aqueous polyurethane compositions and polyurethane-acrylic compositions, revealed by United States Patent Application Publication No. 2010/0330375, can provide a clean high quality dispersion (low in sediment) that quickly self-crosslinks at ambient or low temperatures. Additionally, they are storage stable, have good color stability, and can be formulated with a low volatile organic component content and use significant amounts of renewable raw materials as building blocks.

The main building block of the waterborne polyurethane and urethane-acrylic dispersions, disclosed by United States Patent Application Publication No. 2010/0330375, is a polyketone polyol obtained from the reaction of levulinic acid with epoxidized or epoxy functional natural oils, such as epoxidized soybean oil or epoxidized linseed oil. These oils offer the advantage of being renewable agricultural products. United States Patent Application Publication No. 2010/0330375 further indicates that veronica oil, which is a naturally occurring oil that contains epoxy functional groups, can be used as an alternative. It is well documented that levulinic acid is a significant renewable raw material which can be obtained from biomass in the so called "Biofine Process". Both epoxidized soybean oil and epoxidized linseed oil are commercially available and are widely used as plasticizers for polyvinyl chloride. They, additionally, can act as a scavenger for hydrochloric acid which is liberated when polyvinyl chloride is heat treated. In any case, the polyurethane-acrylate compositions described by United States Patent Application Publication No. 2010/0330375 offer an excellent combination of characteristics and are made using a significant amount of renewable raw materials as building blocks. However, these polyurethane-acrylate compositions are relatively expensive and a lower cost alternative is needed which offers similar performance characteristics and which is derived to a significant extent from renewable resources.

SUMMARY OF THE INVENTION

The present invention provides an economical route to environmentally friendly polymeric coatings with a high content of raw materials from renewable resources. These polymeric coatings also offer performance characteristics that are competitive with conventional coating systems. The unique polymers, on which this invention is based, are copolymers of triglyceride oils, such as soybean oil, linseed oil, or some other natural oil, with a vinyl compound, such as an acrylate or methacrylate, and a vinyl aromatic monomer, such as styrene. The unique polymers do not require diisocyanates or polyisocyanates, which are not biorenewable, to build their molecular weight but instead can be free radically reacted into polymers that compete in performance with urethanes and urethane hybrids.

The stabilization of colloids formed comes mainly from a modified natural oil and can also be supplemented with vinyl colloid stabilizing groups or from external surfactants. The copolymers can either be high in natural oil content or high in vinyl content, depending on the intended end use. Moreover, a variety of functionality can be incorporated into the copolymer dispersions either through the natural oil and/or the vinyl component, including self-crosslinking functionality.

The present invention more specifically, discloses a water dispersible, self-crosslinkable prepolymer composition which is comprised of a triglyceride oil having appended thereto (1) hydroxyl groups, (2) moieties which contain at least one aldehyde group or at least one ketone group, (3) moieties which contain at least one vinyl and/or substituted vinyl group, and (4) optionally, epoxy groups. In one embodiment of this invention the moiety which contains at least one vinyl and/or substituted vinyl group is derived from maleic anhydride.

The subject invention also reveals an aqueous self-crosslinkable copolymer dispersion which is comprised of water and a triglyceride oil having appended thereto (1) hydroxyl groups, (2) moieties which contain at least one aldehyde group or at least one ketone group, (3) moieties which contain at least one carboxyl group or salt thereof, and (4) optionally, epoxy groups. Such aqueous self-crosslinkable copolymer dispersions can be further comprised of an ionizing base. In such aqueous self-crosslinkable copolymer dispersions, the triglyceride oil can additionally contain moieties having at least one vinyl group appended thereto.

DETAILED DESCRIPTION OF THE INVENTION

Figure 1:
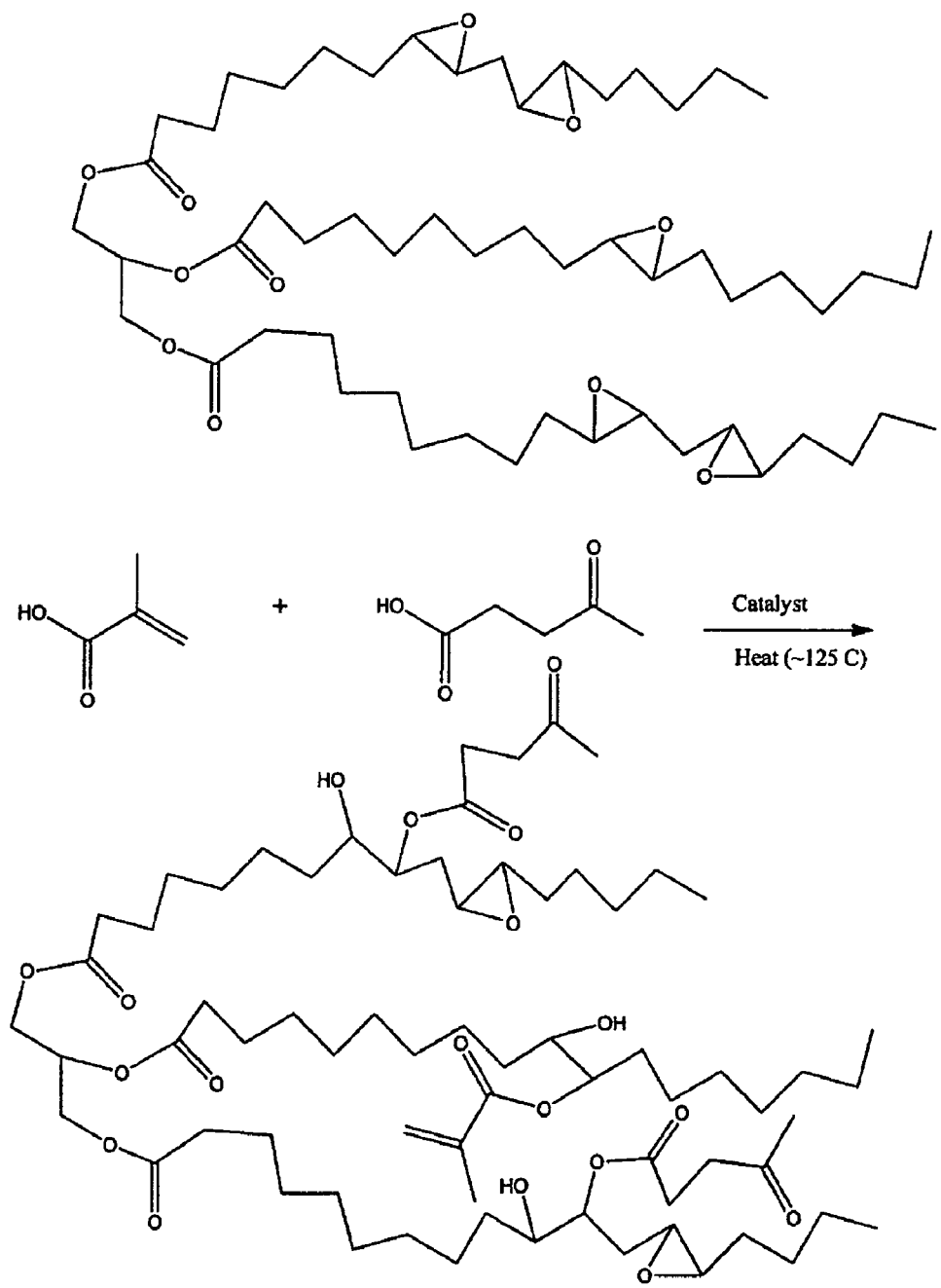
FIG. 1 illustrates the synthesis of a prepolymer (not functionalized yet for water-dispersibility) or macromonomer which utilizes an epoxidized triglyceride oil, such as epoxidized soybean oil, as the starting material. This reaction is carried out by reacting the epoxidized triglyceride oil with (1) a ketone functionalized carboxylic acid or an aldehyde functionalized carboxylic acid, and (2) optionally, a vinyl functionalized carboxylic acid.

The water dispersible, self-crosslinkable prepolymer compositions of this invention are comprised of a triglyceride oil having appended thereto (1) hydroxyl groups, (2) moieties, which contain at least one aldehyde group or at least one ketone group, (3) moieties, which contain at least one vinyl and/or substituted vinyl group, and (4) optionally, epoxy groups, The term vinyl group is typically used to define a group with alpha-beta unsaturation wherein the two carbons of the alpha-beta unsaturation have jointly appended to them three hydrogen atoms. Applicant is defining substituted vinyl groups as groups derived from unsaturated aliphatic anhydrides of di or polycarboxylic acids such as maleic anhydride or itaconic anhydride and/or $C_{1-4}$-alkyl substituted acrylic acids. In one embodiment the substituted vinyl groups are derived from reacting the unsaturated aliphatic anhydrides or di or polycarboxylic acid directly with a hydroxyl group attached directly to a carbon of the triglyceride oil or to an epoxy functionality that comprises an oxygen atom and two carbon atoms of the triglyceride oil. In this embodiment there are no polyether linkages between the triglyceride oil and the vinyl groups. In this context Applicant is defining substituted vinyl as being free radically copolymerizable with vinyl monomers such as where one of more of the three hydrogens are replaced by $C_{1-4}$-alkyl groups (such as derived from methacrylic acid) and/or carboxylic or $C_{1-4}$-alkyl carboxylic groups such as derived from maleic anhydride or itaconic anhydride. This prepolymer composition is made by reacting an epoxidized triglyceride oil with a ketone or aldehyde functionalized carboxylic acid and vinyl group containing carboxylic acid. This reaction is illustrated in FIG. 1 and is normally carried out in the presence of a catalyst at an elevated temperature which is typically within the range of about 100° C. to about 150° C. In most cases, it is preferred for this reaction to be conducted at a temperature which is within the range of 120° C. to about 135° C. Zinc, zirconium, chromium, and iron catalysts can be used advantageously in carrying out this reaction. Some additional examples of catalysts that can be used include trialkylamines, phosphines such as triphenylphosphine, and imidiazoles, such as N-methylimidazole, and the like.

The triglyceride oils that can be utilized as a starting material are unsaturated vegetable oils, animal fats, or synthetic triglycerides, which are generally considered to be derived from condensation reactions of various fatty acids and glycerol. While the triglycerides are often described as oils, they may be solids at room temperature. The higher the amount of unsaturation present, the higher the degree of epoxidation possible under similar reaction conditions. Reactions of these unsaturated oils with strong oxidizers can convert the carbon to carbon double bond in the fatty acids to epoxides. Peracetic acid is a strong oxidizer that can be used for this purpose. The peracetic acid can be obtained from the reaction of acetic acid with hydrogen peroxide. Acetic acid can be obtained from the well-known process of bacterial fermentation.

Epoxidized vegetable oils are commercially available from a number of sources, including companies such as Dow Chemical and Chemtura. The oxirane oxygen content is generally within the range of about 2 to 14 weight percent and is typically within the range of 5 to 12 weight percent before reaction with the ketone or aldehyde functionalized carboxylic acid. It is, typically, preferred to employ an epoxidized triglyceride oil having an oxirane oxygen content which is within the range of 6 to 10 weight percent. The oxirane oxygen value is determined by a nonaqueous potentiometric titrimetry using perchloric acid in the presence of tetraethylammonium bromide. The epoxidized triglyceride oil can have an unsaturated backbone or it can be saturated. It should be noted that epoxidized soybean and linseed oils are both used as plasticizers and sometimes as acid scavengers for polyvinyl chloride.

The ketone or aldehyde functionalized carboxylic acid utilized will normally be of the formula:

wherein A represents a hydrocarbyl moiety containing from 1 to 20 carbon atoms and wherein R represents a hydrogen atom or an alkyl group containing from 1 to 8 carbon atoms. The ketone or aldehyde functionalized carboxylic acid will typically be of the formula:

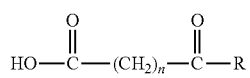

wherein n represents an integer from 1 to 8 and wherein R represents a hydrogen atom or a methyl group. In most cases, n will represent an integer from 2 to 4 with n typically representing 2.

A preferred ketone or aldehyde containing carboxylic acid is levulinic acid (γ-ketovaleric acid; acetylpropionic acid, 4-oxopentanoic acid) or pyruvic acid (α-ketopropionic acid; acetylformic acid). The proportion of carbonyl functional groups in the free radically polymerized polymer (if such is present) is preferably 3 to 200 milliequivalents per 100 g polymer (more preferably 6 to 100 milliequivalents per 100 g polymer). It is possible to use ketone functional diols or polyols from synthetic sources in combination with those obtained from mainly renewable raw materials.

In cases where vinyl group containing carboxylic acids are utilized in making the prepolymer of this invention, they will normally be of the structural formula:

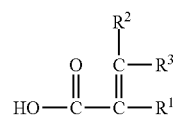

wherein $R^1$, $R^2$, and $R^3$ can be the same or different and represent hydrogen atoms or alkyl groups containing from 1 to 8 carbon atoms. Preferred vinyl group containing carboxylic acids include acrylic acid, methacrylic acid, ethacrylic acid, and the like.

Figure 2:
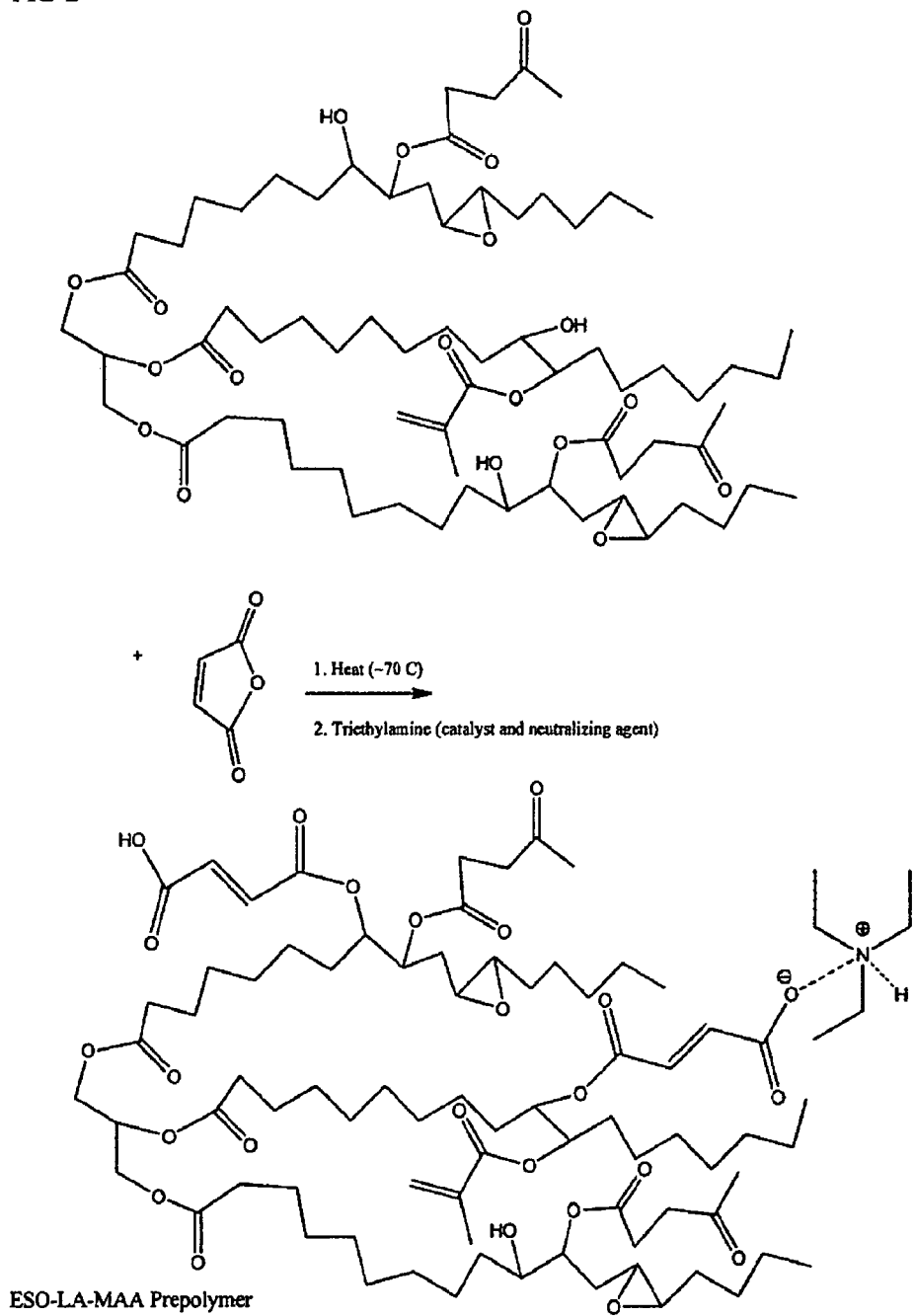
FIG. 2 illustrates the synthesis of a water dispersible self-crosslinkable prepolymer which utilizes the non-dispersible prepolymer of this invention, as described in FIG. 1, as a starting material. In this reaction, the non-dispersible prepolymer is reacted with an anhydride to prepare a water dispersible prepolymer. This reaction can be conducted using a trialkyl amine, such as triethyl amine, both as a catalyst and as a neutralizing agent. The preferred anhydrides for utilization are maleic anhydride and itaconic anhydride, by virtue of ease of processability and providing unsaturation, such as vinyl and/or substituted vinyl groups. This reaction can be carried out at a moderate temperature, such as a temperature which is less than 90° C. It is often desirable to conduct this reaction in the presence of a diluent, such as acetone, methyl ethyl ketone, or a vinyl monomer, to maintain an easily workable viscosity. It is preferable to use a vinyl monomer as the diluent by virtue of the fact that it eventually is copolymerized with the prepolymer and accordingly plays two important roles.

In one embodiment, the synthesis of the water dispersible, self-crosslinkable prepolymer composition involves the reaction of the epoxidized vegetable oil with a ketone or aldehyde functionalized carboxylic acid and then reaction with an anhydride, such as maleic anhydride, to produce an aqueous self-crosslinkable copolymer dispersion, optionally in the presence of a catalyst. A diluent, such as acetone, methyl ethyl ketone, or preferably a vinyl monomer, is normally added to keep the viscosity within a commercially acceptable range. This reaction is depicted in FIG. 2 and is normally conducted at an elevated temperature in the presence of a catalyst. The catalyst can be a tertiary amine (such as a trialkylamine), a phosphonium compound, an inorganic metal salt, a metal alkoxide or a metal chelate. Some representative examples of catalysts that can be used include trimethylamine, triethylamine, tri-n-propylamine, tri-isopropylamine, tri-n-butylamine, tri-t-butylamine, pyridine, isoquinoline, quinoline, N,N-dimethylcyclohexylamine, N-ethylmorpholine, dimethylaniline, dimethylbenzylamine, alkoxides, chelates, or halides of Al, B, Be, Fe(III), Sb(V), Sn, Ti, Zr, and Zn, and the like. It is typically preferred to utilize a trialkylamine, such as triethylamine, as the catalyst since they act both as a catalyst and as an ionizing base.

The anhydrides of di or polycarboxylic acids that can be utilized in preparing the water dispersible prepolymer can be aliphatic or aromatic. Some representative examples of such anhydrides include maleic anhydride, itaconic anhydride, succinic anhydride, phthalic anhydride, pyromellitic anhydride, mellitic anhydride, trimellitic anhydride, and the like. The preferred anhydrides for this use are maleic anhydride, itaconic anhydride, succinic anhydride, trimellitic anhydride, and phthalic anhydride. The most preferred anhydrides are maleic anhydride and itaconic anhydride. These anhydrides, after a ring opening reaction, as depicted in FIG. 2, can function as a dispersing agent for the water dispersible prepolymer after being ionized. In an alternative embodiment of this invention, an external surfactant is utilized as a dispersing agent.

The water dispersible, self-crosslinkable prepolymer composition will generally have a number average molecular weight which is within the range of about 1,500 to about 19,000. The said prepolymer will typically have a number average molecular weight which is within the range of about 2,000 to 9,000, and will more typically have a number average molecular weight which is within the range of about 2,500 to about 5,000. The higher molecular weight can result from coupling multiple epoxidized oils (e.g., though ester linkages from the carboxylic acid groups of the maleic anhydride) into a prepolymer.

The moieties, which contain at least one aldehyde group or at least one ketone group, are of the formula:

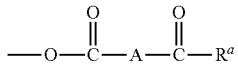

wherein A represents a hydrocarbyl moiety containing from 1 to 20 carbon atoms and wherein $R^a$ represents a hydrogen atom or an alkyl group containing from 1 to 8 carbon atoms. In many cases these moieties are of the formula:

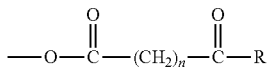

wherein n represents an integer from 1 to 8 and wherein R represents a hydrogen atom or a methyl group. In most cases, n will represent an integer from 2 to 4 with n typically representing 2.

The moieties, which contain at least one vinyl and/or substituted vinyl group, are of a formula selected from the group consisting of:

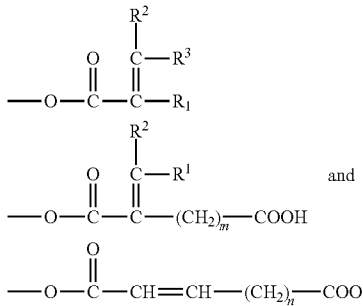

or are a mixture of such moieties, wherein m represents an integer from 0 to 8, and wherein $R^1$, $R^2$, and $R^3$ can be the same or different and represents hydrogen atoms or alkyl groups containing from 1 to 8 carbon atoms. In most cases, m will represent in integer from 0 to 4 with m typically being 0. Normally, on average from 1 to about 4 functional groups will be appended to each molecule of triglyceride oil with it being more typical for 2 or 3 functional groups to be appended to each molecule of triglyceride oil. In one embodiment of this invention, the prepolymer is neutralized by reaction with at least one neutralizing agent and dispersed in aqueous medium.

Various additional monomers can optionally be copolymerized with the prepolymer. For instance, the acrylic polymer or copolymer can be derived from a variety of unsaturated monomers such as from acrylate, alkyl (alk) acrylate, vinyl chloride, vinylidene chloride, vinyl acetate, styrene, butadiene, and unsaturated acid containing monomers. The various alkyl acrylates (or esters of acrylic acid) are of the formula:

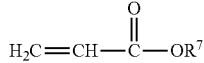

wherein $R^7$ is an alkyl group containing 1 to about 15 carbon atoms, an alkoxyalkyl group containing a total of 1 to about 10 carbon atoms, a cyanoalkyl group containing 1 to about 10 carbon atoms, or a hydroxy alkyl group containing from 1 to about 18 carbon atoms. The alkyl structure can contain primary, secondary, or tertiary carbon configurations and normally contains 1 to about 10 carbon atoms with 2 to 8 carbon atoms being preferred. Examples of such acrylic esters include methyl acrylate, ethyl acrylate, propyl acrylate, n-butyl acrylate, isobutyl acrylate, n-pentyl acrylate, isoamyl acrylate, n-hexyl acrylate, 2-methylpentyl acrylate, n-octyl acrylate, 2-ethylhexyl acrylate, n-decyl acrylate, n-dodecyl acrylate, n-octadecyl acrylate, and the like. Preferred examples include ethylacrylate, butyl acrylate, 2-ethyl hexyl acrylate, and the like.

The various alkyl alkacrylates (or esters of alkacrylic acid) are of the formula:

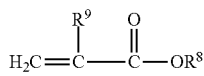

wherein $R^8$ is an alkyl group containing 1 to about 15 carbon atoms, an alkoxyalkyl group containing a total of 1 to about 10 carbon atoms, a cyanoalkyl group containing 1 to about 10 carbon atoms, or a hydroxy alkyl group containing from 1 to about 18 carbon atoms (as described above) and wherein $R^9$ is an alkyl containing from 1 to about 4 carbon atoms, desirably, 1 or 2 carbon atoms with methyl being especially preferred. Examples of various alkyl (alk)acrylates include methyl methacrylate, ethyl methacrylate, methoxymethyl acrylate, methoxyethyl acrylate, ethoxyethyl acrylate, butoxy ethyl acrylate, ethoxypropyl acrylate, and the like. Derivatives include hydroxyethyl acrylate, hydroxypropyl acrylate, hydroxybutyl acrylate, and the like. Mixtures of two or more of the above monomers can also be utilized.

Unsaturated acid containing monomers include acrylic acid, methacrylic acid, itaconic acid, maleic acid, fumaric acid, 2-carboxyethyl acrylate and the like. Acrylic acid is preferred. Half esters of the above di-carboxylic acids can also be used as monomers wherein the ester portion is desirably an alkyl having from 1 to about 10 carbon atoms and specific examples include mono methyl maleate, mono methyl fumerate, mono methyl itaconate, and the like.

Other co-polymerizable (ethylenically unsaturated) monomers may be utilized to make copolymers including styrenic monomers (as a co-monomer in the acrylate latex), vinyl chloride type monomers, acrylonitrile type monomers, various vinyl ester monomers, various acrylamides monomers, various alkynol acrylamides and the like. Considering the styrenic monomers (as both a primary monomer in styrene-butadiene polymers or a co-monomer in acrylate polymers), they are often referred to as vinyl substituted aromatic compounds (styrenic monomers) and include styrene, alkyl substituted styrene 1-vinylnaphthalene, 2-vinylnaphthalene, and the alkyl, cycloalkyl, aryl, alkaryl and aralkyl derivatives thereof, in which the total number of carbon atoms, in the combined, substituents is generally from 8 to about 12. Examples of such compounds include 3-methylstyrene vinyltoluene; alpha-methylstyrene; 4-n- propylstyrene, 4-t-butylstyrene, 4-dodecyl-styrene, 4-cyclohexylstyrene; 2-ethyl-4-benzylstyrene; 4-methoxy-styrene; 4-dimethylaminostyrene; 3,5-diphenoxystyrene; 4-p-tolylstyrene; 4-phenylstyrene; 4,5-dimethyl-1-vinylnaphthalene; 3-n-propyl-2-vinylnaphthalene, and the like. Styrene is typically preferred.

The vinyl chloride type monomers include vinyl chloride, vinylidene chloride, and the like.

The vinyl esters can generally be represented by the formula:

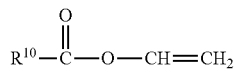

wherein $R^{10}$ is an alkyl group generally having from 1 to about 10 or 12 carbon atoms with from about 1 to about 6 carbon atoms being preferred. Accordingly, suitable vinyl esters include vinyl formate, vinyl acetate, vinyl propionate, vinyl butyrate, vinyl valerate, and the like. Vinyl esters with larger $R^{10}$ groups include the vinyl versatate monomers, such as Veo VA-P, Veo Va-10, and Veo Va-11.

The various vinyl ethers can be represented by the formula:

wherein $R^4$ is desirably an alkyl having from 1 to about 10 carbon atoms. Specific examples include methyl vinyl ether, ethyl vinyl ether, butyl vinyl ether, and the like with methyl vinyl ether being preferred.

The acrylonitrile type monomers that can be utilized include acrylonitrile, or methacrylonitrile, or ethacrylonitrile, and the like. The acrylamide monomers which can be polymerized to form a copolymer generally have the following formula:

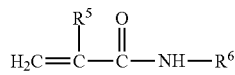

wherein $R^5$ represents a hydrogen atom or a methyl group and wherein $R^6$ is represents a hydrogen atom or an alkyl group (straight chained or branched) containing from 1 to about 18 carbon atoms. Specific examples include acrylamide, ethyl acrylamide, butyl acrylamide, tert-octyl acrylamide, tert-butyl methacrylamide, and the like. Unlike the other optional monomers the one or more acrylamides can be utilized in large amounts such as up to about 20 percent by weight of the copolymer and desirably from about 0.5 to about 10 percent by weight.

Functionalized acrylamides can also be utilized. Examples of such acrylamides include AMPS, i.e., 2-acrylamido-2-methylpropanesulfonic acid, DMAPMA, i.e., dimethylaminopropyl methacryamide, and the like.

Carbonyl containing unsaturated comonomers may be copolymerized with the above monomers to make acrylic or vinyl polymers. Examples of carbonyl-containing monomers, which may be mentioned, include acrolein, methacrolein, diacetoneacrylamide, crotonaldehyde, 4-vinylbenzaldehyde, vinyl alkyl ketones of 4 to 7 carbon atoms such as vinyl methyl ketone, and acryloxy- and methacryloxy-alkyl propanols of formula $H_2C=C(R^3)-C(O)-O-C(R^{11})H-C(R^{12})(R^9)-C(O)H$ where R represents a hydrogen atom or a methyl group, $R^{11}$ is H or alkyl of 1 to 3 carbon atoms, $R^{12}$ is alkyl of 1 to 3 carbon atoms, and $R^9$ is alkyl of 1 to 4 carbon atoms. Further examples include acrylamidopivalaldehyde, methacrylamidopivalaldehyde, 3-acrylamidomethyl-anisaldehyde, diacetone acrylate, acetonyl acrylate, diacetone methacrylate, acetoacetoxyethylmethacrylate, 2-hydroxypropylacrylate acetylacetate, and butanediolacrylate acetylacetate. More details on using these monomers are provided in U.S. Pat. No. 4,983,662. The teachings of U.S. Pat. No. 4,983,662 are incorporated herein by reference for the purpose of describing the use of such monomers in greater detail.

In one embodiment, the vinyl monomers, described above, can be intentionally grafted or copolymerized with the water dispersible prepolymer component of this invention by using active hydrogen containing vinyl monomers in the formation of the prepolymer or the vinyl polymers. Examples of such active hydrogen containing vinyl monomers include 2-hydroxyethyl acrylate (2HEA) and 2-hydroxyethyl methacrylate (2HEMA).

Conventionally free radical initiators, known to the art and to the literature, can be utilized to initiate polymerization of the various above-noted monomers or comonomers to form a polymer or copolymer. Such free radical initiators, generally, include the persulfates, the peroxides, and azo compounds, as well as redox combinations and radiation sources. Examples of preferred persulfate initiators include potassium persulfate, sodium persulfate, or ammonium persulfate, and the like. The free radical polymerization can be an emulsion, bulk, solution, or dispersion polymerization.

Generally, any type of peroxide, azo, redox system, or related initiator system can be utilized. Peroxide systems include dicumyl peroxide, cumene hydroperoxide, t-butyl perbenzoate, bis(t-butylperoxy)diisopropyl benzene, diisopropyl benzene hydroperoxide and n-butyl 4,4-bis(t-butylperoxy)valerate, as well as benzoyl peroxide, and t-butyl hydroperoxide, and the like. Cumene hydroperoxide, t-butyl hydroperoxide and diisopropyl benzene hydroperoxide are preferred. Azo initiators include 2,2'-azobis(isobutyronitrile) (AIBN) and related azo initiators.

Polymers or copolymers, can be made by utilizing chain-transfer agents/polymer physical property modifiers. Conventional chain-transfer agents can be utilized, such as, various mercaptans, for example, thioethanol mercaptan, hydroxylethyl mercaptan, various reaction products of alkyl esters of mercaptan with acidic acid or with thiogylcolic acid, and the like wherein the alkyl group has from about 2 to about 20 carbon atoms. Another suitable chain transfer agent is beta mercapto propionic acid and its esters such as butyl-3-mercaptoproprinate. Examples of chain transfer agents can include dithiocarbamates or di or trithiocarbonates.

Once the prepolymer is formed, it is dispersed in an aqueous medium to form a dispersion. Dispersing the prepolymer in aqueous medium can be done by any conventional technique, in the same way that polyurethane prepolymers made by bulk or solution polymerization are dispersed in water as described in United States Patent Application Publication No. 2010/0330375 A1. The teachings of United States Patent Application Publication No. 2010/0330375 A1 are incorporated herein by reference. Normally, this will be done by combining the prepolymer blend, with water with mixing. Where solvent polymerization is employed, the solvent and other volatile components can optionally be distilled off from the final dispersion, if desired. The hydrazine functional moiety, for crosslinking with the ketone group, can be added at this stage or later.

The preferred hydrazine functional moiety refers to a low molecular weight molecule or oligomers having one or more hydrazine or hydrazone groups. By a hydrazine functional group is meant the functional group of formula —NHNH$_2$. In the practice of this invention, the hydrazone functional group is a group derived from such a hydrazine group by reaction with a monoketone or monaldehyde containing at least 2 carbon atoms. Hydrazine functional moieties can also be dihydrazides and other polyhydrazides, as expressed below, in that these molecules have the specified —NHNH$_2$ group.

While hydrazine itself (H$_2$N—NH$_2$) at elevated concentrations, raises concerns about worker exposure, hydrazide (—NHNH$_2$) containing molecules are less of an exposure issue and offer the opportunity to build molecular weight and/or crosslink molecules/oligomers/polymers after polyurethane dispersion coagulation/film formation at or around room temperature. Volatile amines can play a significant role in the reactions using hydrazine functional moieties as the amines are/can be used in polyurethane dispersions to adjust the pH to the basic side before coalescence and allow the pH to shift to the acid side as the water and volatile amines evaporate. This pH shift and water evaporation promotes the reaction of hydrazine groups with available ketone or aldehyde groups (providing molecular weight buildup and or crosslinking).

In one embodiment of the invention, where the prepolymer includes enough water-dispersibility enhancing compound to form a stable dispersion without added emulsifiers (surfactants), the dispersion can be made without such compounds, i.e., substantially free of surfactants, if desired. In one embodiment of this invention a surface active agent, such as a sulfate or a phosphate, can beneficially be included in the prepolymer composition.

In those instances in which the prepolymer includes water-dispersibility enhancing compounds which produce pendant carboxyl groups, these carboxyl groups can be converted to carboxylate anions for further enhancing the water-dispersibility of the prepolymer. A typical way the dispersions of the present invention can be made is by forming a prepolymer blend in the substantial absence of water and then dispersing the blend in an aqueous medium with mixing. Other ways of making aqueous dispersions can also be used to make the dispersions of this invention, including shear mixing, the acetone process, the continuous process polymerization, and the reverse feed process.

It is frequently desirable to include a bisulfite or sulfite to improve the stability of the dispersion. For instance, sodium sulfite, potassium sulfite, ammonium sulfite, calcium sulfite, magnesium sulfite, zinc sulfite, sodium bisulfite, potassium bisulfite, ammonium bisulfite, calcium bisulfite, magnesium bisulfite, or zinc bisulfite can be included in the dispersion. The sulfite or bisulfite will typically be added to the dispersion in a post polymerization step because it can interfere with the polymerization by acting as a chain transfer agent. In any case, the sulfite or bisulfite will typically not be added in more than a stoichiometric amount, based upon the number of ketone groups in the polymer. The sulfite or bisulfite will typically be added at a level which is within the range of 0.1 weight percent to 0.5 weight percent, based upon the solids content of the dispersion.

In shear mixing the prepolymer is dispersed by shear forces with emulsifiers (external emulsifiers, such as surfactants, or internal emulsifiers having nonionic, anionic, cationic and/or zwitterionic groups as part of or pendant to the polymer backbone, and/or as end groups on the polymer backbone).

In the acetone process a prepolymer is formed with or without the presence of acetone, MEK, and/or other polar solvents that are non-reactive and easily distilled. The prepolymer is further diluted in said solvents as necessary, and optionally chain extended with an active hydrogen-containing compound. Water is added and then the solvents are distilled off.

In the continuous process polymerization procedure a prepolymer is formed and then pumped through high shear mixing head(s) and dispersed into water. This is accomplished by multiple streams consisting of prepolymer (or neutralized prepolymer), optional neutralizing agent, water, and/or surfactant.

In the reverse feed process water and optional neutralizing agent(s) and/or extender amine(s) are charged to the prepolymer under agitation. The prepolymer can be neutralized before water is added.

The aqueous self-crosslinkable copolymer dispersion can then optionally be diluted with additional water to any concentration (solids content) that is desired. The aqueous self-crosslinkable copolymer dispersion can then be used in the preparation of water based coatings and inks, such as paints, varnishes, clear-coats, ink jet inks, and paper coatings, employing techniques that are well-known to those skilled in the art. Desired pigments, plasticizers, coalescing solvents, fillers, wetting agents, stabilizers, defoamers, dryers, antibacterial agents, fungicides, insecticides, antifouling agents, and anticorrosive agents can be mixed directly into the aqueous self-crosslinkable copolymer dispersion.

Pigments are normally added to paint formulations to impart color and hiding to the coating. Titanium dioxide is an example of a widely used pigment which imparts hiding and a white color. Mineral pigments (such as oxides of iron and chromium), organic pigments (such as phthalocyanine) and active anticorrosive pigments (such as zinc phosphate) are representative examples of other widely used pigments.

The fillers employed in making water based coating formulations are normally inexpensive materials which are added to attain the desired consistency and non-settling characteristics. Fillers can also improve a coating's physical properties, such as resistance to cracking and abrasion. Some representative examples of widely utilized fillers include chalks, clays, micas, barites, talcs, and silica.

Fungicides and algaecides are commonly added to interior and exterior house paints and are of particular value in coating formulations that will be used in warm climates. Antifouling compounds are commonly added to marine paints to inhibit marine growth.

A film forming, water based composition can be prepared utilizing a mixture of the aqueous self-crosslinkable copolymer dispersion with a suitable coalescing solvent and plasticizer. It is preferred for the coalescing solvent to be at least water immiscible and, even more preferably, for it to be water insoluble. Of the various solvents which can be used, generally, ethylene glycol monobutyl ether, ethylene glycol monoethyl ether, diethylene glycol monomethyl ether, diethylene glycol monoethyl ether, diethylene glycol monobutyl ether, propylene glycol monobutyl ether, propylene glycol monoethyl ether, dipropylene glycol monomethyl ether, dipropylene glycol monoethyl ether, and/or dipropylene glycol monobutyl ether are preferred. It should be noted that the solvent and plasticizer can be mixed directly with the resin in its water emulsion.

Plasticizers are used to control the hardness of the coating and/or to impart flexibility. Poor adhesion can be encountered when water based coatings are applied to some substrates. Adhesion can frequently be improved by the addition of one or more plasticizers to the water based coating formulation.

Of the various plasticizers, it is desired that one be selected which is liquid at room temperature such as 25° C. and have a sufficiently high boiling point, preferably at least 100° C., and even more preferably, at least 150° C., so that they do not volatilize from the coating composition when applied to a substrate. The plasticizer should enhance the water insolubility of a dried coating of the coalesced resin. It is important for the plasticizer, or mixture of plasticizers, to be compatible with the resin itself.

A wide variety of plasticizers can be used in the practice of this invention. They can, for example, be of the type listed in the Federation Series on Coatings Technology, Unit Twenty-two, entitled "Plasticizers," published April, 1974, so long as they fulfill the melting point, boiling point and compatibility requirements. Some representative examples of plasticizers that can be used include propylene glycol methyl ether, dipropylene glycol methyl ether, tripropylene glycol methyl ether, propylene glycol methyl ether acetate, dipropylene glycol methyl ether acetate, propylene glycol n-propyl ether, dipropylene glycol n-propyl ether, propylene glycol n-butyl ether, dipropylene glycol n-butyl ether, tripropylene glycol n-butyl ether, propylene glycol phenyl ether, propylene glycol diacetate, dipropylene glycol dimethyl ether, diethylene glycol ethyl ether, diethylene glycol methyl ether, diethylene glycol n-butyl ether, diethylene glycol hexyl ether, diethylene glycol n-butyl ether acetate, ethylene glycol propyl ether, ethylene glycol n-butyl ether, ethylene glycol hexyl ether, ethylene glycol n-butyl ether acetate, triethylene glycol methyl ether, triethylene glycol ethyl ether, triethylene glycol n-butyl ether, ethylene glycol phenyl ether, ethylene glycol n-butyl ether mixture, polyethylene glycol dibenzoate, ortho and/or para-toluene sulfonamide, trimethylpentanediol dibenzoate and trimethylpentanediol monoisobutyrate monobenzoate.

In making the water based coating compositions of this invention, typically, the self-crosslinkable copolymer will be added at a level which is sufficient to attain a solids content which is within the range of about 25 weight percent to about 70 weight percent. The solids content will, preferably, be within the range of 30 weight percent to 60 weight percent and will, typically, be within the range of about 40 weight percent to 55 weight percent. However, more or less water can usually be employed depending upon whether a high or low viscosity dispersion or solution is desired and depending upon whether high or low solids content is desired. Level of resin utilized will also depend upon the type and amount of coalescing solvent and plasticizer used. The water reduced coating composition, as an aqueous dispersion or solution, can then be applied as a coating onto a suitable substrate such as wood, masonry, plastic or metals. The water based coating compositions of this invention are a particular value for application to wood surfaces, such as wood flooring surfaces.

Desirably, the reaction between the ketone group of the prepolymer and hydrazine functional moiety is delayed until after particle coagulation and coalescence, but the technology is not limited thereby. Desirably, the ketone group and the hydrazine functional moiety react to form azomethine linkages as taught in U.S. Pat. No. 4,210,565 and U.S. Pat. No. 4,983,662, the teachings of which are incorporated herein by reference. Desirably, this reaction between the ketone groups of the prepolymer and the hydrazine functional moiety proceeds at a reasonable rate at 20° C. to 25° C. such that lower molecular weight species associated with these moieties are converted at 20° C. to 25° C. (ambient drying temperature) to higher molecular weight and/or crosslinked species that aid rather than detract from polymer hardness, strength, solvent resistance, and related properties of wear resistance.

This invention is illustrated by the following examples that are merely for the purpose of illustration and are not to be regarded as limiting the scope of the invention or the manner in which it can be practiced. Unless specifically indicated otherwise, parts and percentages are given by weight.

Some materials, listed as item 1, (such as the reaction product of epoxidized soybean oil (ESO such as Jenkinol™ 680 from Acme Hardesty or Plasthall™ ESO from Hallstar) with organic carboxylic acids, typically levulinic acid (LA) and methacrylic acid (MAA)), was done separately in a large batch and aliquots were used to conduct/prepare several experimental dispersions. Thus, in some examples, only the weight of the "ESO-LA-MAA" reaction product is shown and not the individual components; although the equivalents of the organic carboxylic acid reactants are indicated. In a larger scale-up or commercial production setting, this reaction of ESO with various organic carboxylic acid reactants such as LA and MAA could be done sequentially in the same reactor as the final prepolymer; this would be the most efficient route for commercial production.

Example 1

Soy Oil Polyol Functionalized with Ketone

A poly-ketone functional oligomer was prepared by combining items 1-3 of the ingredients below in a 4 neck flask equipped with a thermometer, overhead stirrer and nitrogen gas inlet. With stirring and under a nitrogen blanket, the temperature of the reaction mixture was raised to 110° C. to 114° C. and held at this temperature for 1 hour. The temperature was then raised to 121-125° C. and held at this temperature for four hours or until the acid number was <1.0 (mg KOH/g). The final material was clear with an emerald green tint and a viscosity of ~1,800 cps at 70° C. at an acid number of 0.98 mg KOH/g.

| Item # | Material | Parts |
|---|---|---|
| 1 | Epoxidized Soybean Oil | 298.0 |
| 2 | Levulinic Acid | 92.6 |
| 3 | Cr(III)Acetate (as a 20% solution in levulinic acid) | 0.5 |

Example 2

Soy Oil Polyol Functionalized With Ketone/Acrylate

A poly(ketone/acrylate) functional oligomer was prepared by combining items 1-5 of the ingredients below in a 4 neck flask equipped with a thermometer, overhead stirrer and dry air inlet. With stirring and under a nitrogen blanket, the temperature of the reaction mixture was raised to 110° C. to 114° C. and held at this temperature for 1 hour. The temperature was then raised to 121-125° C. and held at this temperature for at least 2 hours or until the acid number was <1.0 (mg KOH/g). The final material was clear with an emerald green tint and a viscosity of ~1,730 cps at 70° C. at an acid number of 0.7 mg KOH/g.

| Item # | Material | Parts |
|---|---|---|
| 1 | Epoxidized Soybean Oil | 303.0 |
| 2 | Levulinic Acid | 68.8 |
| 3 | Methacrylic acid | 16.6 |
| 4 | BHT | 0.2 |
| 5 | Cr(III)Acetate (as a 20% solution in levulinic acid) | 0.42 |

Example 3

Soy Oil Polyol Functionalized with Ketone

A poly-ketone functional oligomer was prepared by combining items 1-3 of the ingredients below in a 4 neck flask equipped with a thermometer, overhead stirrer and nitrogen gas inlet. With stirring and under a nitrogen blanket, the temperature of the reaction mixture was raised to 110° C. to 114° C. and held at this temperature for 1 hour. The temperature was then raised to 121-125° C. and held at this temperature for 2 hours or until the acid number was <1.0 (mg KOH/g). The final material was clear with a light amber tint and a viscosity of ~1,450 cps at 70° C. at an acid number of 0.8 mg KOH/g.

| Item # | Material | Parts |
|---|---|---|
| 1 | Epoxidized Soybean Oil | 317.5 |
| 2 | Levulinic Acid | 70.5 |
| 3 | Zirconium Propionate (as a 20% solution in levulinic acid) | 0.82 |

Example 4

Poly-Ketone-Methacrylate Functional Soy Oil Polyol

A poly-ketone functional oligomer was prepared by combining items 1-5 of the ingredients below in a 4 neck flask equipped with a thermometer, overhead stirrer and dry air inlet. With stirring and under a nitrogen blanket, the temperature of the reaction mixture was raised to 110° C. to 114° C. and held at this temperature for 1 hour. The temperature was then raised to 121-125 C and held at this temperature for 2 hours or until the acid number was <1.0 (mg/g). The final material was clear with an amber tint and a viscosity of ~1,510 cps at 70 C at an acid number of 0.9 mg/g.

| Item # | Material | Parts |
|---|---|---|
| 1 | Epoxidized Soybean Oil (ESO) | 318.0 |
| 2 | Levulinic Acid (LA) | 53.0 |
| 3 | Methacrylic Acid (MAA) | 13.1 |
| 4 | BHT | 0.3 |
| 5 | Zirconium Propionate (as a 20% solution in levulinic acid) | 1.32 |

Example 5

Soy Oil Polyol Functionalized with Ketone/Acrylate

A poly(ketone/acrylate) functional oligomer was prepared by combining items 1-7 of the ingredients below in a 4 neck flask equipped with a thermometer, overhead stirrer and dry air inlet. With stirring and under a nitrogen blanket, the temperature of the reaction mixture was raised to 110° C. to 114° C. and held at this temperature for 1 hour. The temperature was then raised to 121° C.-125° C. and held at this temperature for 2 hours or until the acid number was <1.0 (mg KOH/g). The final material was clear with an amber tint and a viscosity of ~1,670 cps at 70° C. at an acid number of 0.9 mg KOH/g.

| Item # | Material | Parts |
|---|---|---|
| 1 | Epoxidized Soybean Oil | 234.5 |
| 2 | Levulinic Acid | 39.3 |
| 3 | Methacrylic acid | 17.2 |
| 4 | Dehydrated Castor Fatty Acid | 22.7 |
| 5 | BHT | 0.1 |
| 6 | Cr(III)Acetate (as a 20% solution in levulinic acid) | 1.0 |
| 7 | Zirconium Propionate (as a 20% solution in levulinic acid) | 1.0 |

Example 6

Soy Oil Vinyl Copolymer Dispersion

A prepolymer was prepared by first homogenizing the polyol prepared in Example 1 (Item 1) with maleic anhydride by heating to 70° C. until the solid maleic anhydride is homogenized (melted) into the polyol. At this point the TEA, MMA, styrene and BHT (items 2-6) are added and the mixture held at 70° C. for 20 minutes. After which the mixture was allowed to cool to room temperature and allowed to continue to react over the next 45 minutes. This resulted in a prepolymer with a dark amber color of modest viscosity at room temperature (~22° C.) due to its dilution in MMA and styrene.

| Item # | Material | Parts |
|---|---|---|
| 1 | Reaction product from Example 1 | 47.2 |
| 2 | Maleic Anhydride | 5.0 |
| 3 | Methyl Methacrylate (MMA) | 13.1 |
| 4 | Styrene | 4.4 |
| 5 | Triethylamine (TEA) | 5.1 |
| 6 | BHT | 0.1 |

The resulting prepolymer (70.9 parts) at ~22° C. was dispersed in water having an initial temperature of ~20° C.-22° C. containing ammonia (0.5 parts 28% aqueous) to give a dispersion of a larger particle size with an opaque or milky appearance. Slow addition of ammonia at this point helped to adjust particle size significantly lower to a translucent state with a dark amber tint with low viscosity. Then, 34.2 parts of styrene and 2.0 parts of di-vinyl benzene (DVB 80) was added and allowed to homogenize into the dispersion. The resulting dispersion was free radical polymerized by adding 0.2 parts of a 1% Fe-EDTA and 2.4 parts of 3.5% t-butyl hydrogen peroxide which was allowed to mix into the dispersion prior to slowly adding 3.0 parts of 2.0% erythorbic acid at an initial temperature of 20° C. This resulted in a rather slow/sluggish polymerization of the vinyl functional monomers as evident by an exotherm from 20° C. to 44° C. The vinyl polymerization was chased with a small amount of additional t-butyl hydrogen peroxide and erythorbic acid and applied heat to help complete the conversion of vinyl monomer to polymer. Afterwards, adipic dihydrazide was added to the dispersion to provide a coating with the potential to self-crosslink through a condensation of the hydrazide with ketones on the polymer; the effect of which was observed in a significant increase in hardness and very good mar and black heel mark resistance for the dried coating. The final dispersion was low in sediment with a solids level of 45.7%, a viscosity of 102 cps (at 25° C.) at a pH of 7.2 with a particle size of 40.5 nm.

Example 7

Soy Oil Vinyl Copolymer Dispersion

A prepolymer was prepared by first homogenizing the polyol prepared in Example 2 (Item 1) with maleic anhydride by heating to 70° C. until the solid maleic anhydride is homogenized (melted) into the polyol. At that point the TEA and MMA (items 2 and 3) are added and the mixture held at 70° C. for 20 minutes. After which the mixture was allowed to cool to room temperature and allowed to continue to react over the next 45 minutes. This resulted in a prepolymer with a dark amber color with relatively low viscosity at room temperature (~22° C.) due to its dilution in MMA.

| Item # | Material | Parts |
|---|---|---|
| 1 | Reaction product from Example 2 | 58.3 |
| 2 | Maleic Anhydride | 6.0 |
| 3 | Methyl Methacrylate | 21.6 |
| 4 | Triethylamine | 6.2 |
| 5 | BHT | 0.2 |

The resulting prepolymer (89 parts) at ~22° C. was dispersed in water having an initial temperature of ~20° C.-22° C. containing ammonia (0.5 parts 28% aqueous) to give a dispersion of a small particle size with a clear appearance with a dark amber tint with low viscosity. To the resulting dispersion, 42.8 parts of styrene was added and allowed to homogenize into the dispersion. The resulting dispersion was free radical polymerized by adding 0.2 parts of a 1% Fe-EDTA and 2.0 parts of 3.5% t-butyl hydrogen peroxide which was allowed to mix into the dispersion prior to slowly adding 2.6 parts of 2.0% erythorbic acid at an initial temperature of 20° C. This resulted in a rather slow/sluggish polymerization of the vinyl functional monomers as evident by an exotherm from 20° C. to 34° C. at which point the viscosity increased requiring addition of 20 parts water. The vinyl polymerization was chased with a small amount of additional t-butyl hydrogen peroxide and erythorbic acid and applied heat to help complete the conversion of vinyl monomer to polymer. Afterwards, 4.5 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 42.0%, a viscosity of 69 cps (at 25° C.) at a pH of 7.6 with a particle size of 40.7 nm.

Example 8

Soy Oil Vinyl Copolymer Dispersion

A prepolymer was prepared by first homogenizing the polyol prepared in Example 2 (Item 1) with maleic anhydride by heating to 70° C. until the solid maleic anhydride is homogenized (melted) into the polyol. At this point the TEA and MMA (items 2 and 3) are added and the mixture held at 70° C. for 20 minutes. After which the mixture was allowed to cool to room temperature and allowed to continue to react over the next 45 minutes. This resulted in a prepolymer with a dark amber color of modest viscosity at room temperature (~22° C.) due to its dilution in MMA.

| Item # | Material | Parts |
|---|---|---|
| 1 | Reaction product from Example 2 | 58.3 |
| 2 | Maleic Anhydride | 6.0 |
| 3 | Methyl Methacrylate | 21.6 |
| 4 | Triethylamine | 3.1 |
| 5 | BHT | 0.2 |

The resulting prepolymer (85 parts) at ~22° C. was dispersed in water having an initial temperature of ~20° C.-22° C. containing ammonia (0.5 parts 28% aqueous) to give a dispersion of a larger particle size with an opaque or milky appearance. Slow addition of ammonia, at this point, helped to adjust particle size significantly lower to a translucent state with a dark amber tint with low viscosity. Then, 40.9 parts of styrene and 3.0 parts of di-vinyl benzene (DVB 80) was added and allowed to homogenize into the dispersion. To the resulting dispersion was free radical polymerized by adding 0.2 parts of a 1% Fe-EDTA and 2.4 parts of 3.5% t-butyl hydrogen peroxide which was allowed to mix into the dispersion prior to slowly adding 3.0 parts of 2.0% erythorbic acid at an initial temperature of 20° C. This resulted in a rather slow polymerization of the vinyl functional monomers with an observed exotherm from 20° C. to 39° C. at which point the viscosity increased requiring addition of 30 parts water. As the vinyl polymerization progressed, the particle size decreased as observed in the increased clarity of the dispersion. The vinyl polymerization was chased with a small amount of additional t-butyl hydrogen peroxide and erythorbic acid and applied heat to help complete the conversion of vinyl monomer to polymer. Afterwards, 5.8 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 38.0%, a viscosity of 133 cps (at 25° C.) at a pH of 8.9 with a particle size of 43.0 nm.

Example 9

Soy Oil Vinyl Copolymer Dispersion

A prepolymer was prepared by first homogenizing the polyol, prepared in Example 2 (Item 1), with maleic anhydride by heating to 70° C. until the solid maleic anhydride is homogenized (melted) into the polyol. At this point, the TEA and MMA (items 2 and 3) are added and the mixture held at 70° C. for 20 minutes. After which, the mixture was allowed to cool to room temperature and allowed to continue to react over the next 45 minutes. This resulted in a prepolymer with a dark amber color of modest viscosity at room temperature (~22° C.) due to its dilution in MMA.

| Item # | Material | Parts |
|---|---|---|
| 1 | Reaction product from Example 2 | 58.3 |
| 2 | Maleic Anhydride | 6.0 |
| 3 | Methyl Methacrylate | 21.6 |
| 4 | Triethylamine | 3.1 |
| 5 | BHT | 0.2 |

The resulting prepolymer (85 parts) at about 21° C. was dispersed in water having an initial temperature of ~20° C. containing ammonia (0.5 parts 28% aqueous) to give a dispersion of a larger particle size with an opaque or milky appearance. Slow addition of ammonia, at this point, helped to adjust particle size significantly lower to a translucent state with a dark amber tint with low viscosity. Then, 40.9 parts of styrene, 3.0 parts of di-vinyl benzene (DVB 80), and 1.2 parts of diacetoneacrylamide (as a 20% solution in water) was added and allowed to homogenize into the dispersion. To the resulting dispersion was free radical polymerized by adding 0.2 parts of a 1% Fe-EDTA and 2.4 parts of 3.5% t-butyl hydrogen peroxide which was allowed to mix into the dispersion prior to slowly adding 3.0 parts of 2.0% erythorbic acid at an initial temperature of 20° C. This resulted in a rather slow polymerization of the vinyl functional monomers with an observed exotherm from 20° C. to 41° C.

As the vinyl polymerization progressed the particle size decreased as was confirmed by an observed increase in the clarity of the dispersion. The vinyl polymerization was chased with a small amount of additional t-butyl hydrogen peroxide and erythorbic acid and applied heat to help complete the conversion of vinyl monomer to polymer. Afterwards 6.4 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 42.5%, a viscosity of 88 cps (at 25° C.) at a pH of 7.3, and a particle size of 39.8 nm.

Example 10

Soy Oil Vinyl Copolymer Dispersion

A prepolymer was prepared by first homogenizing the polyol, prepared in Example 2 (Item 1), with maleic anhydride by heating to 70° C. until the solid maleic anhydride is homogenized (melted) into the polyol. At this point the TEA and MMA (items 2 and 3) are added and the mixture held at 70° C. for 20 minutes. After which the mixture was allowed to cool to room temperature and allowed to continue to react over the next 45 minutes. This resulted in a prepolymer with a dark amber color of modest viscosity at room temperature (~22° C.) due to its dilution in MMA.

| Item # | Material | Parts |
|---|---|---|
| 1 | Reaction product from Example 2 | 58.3 |
| 2 | Maleic Anhydride | 6.0 |
| 3 | Methyl Methacrylate | 21.6 |
| 4 | Triethylamine | 1.6 |
| 5 | BHT | 0.1 |

The resulting prepolymer (85 parts) at ~21° C. was dispersed in water having an initial temperature of ~20° C. containing ammonia (3 parts 28% aqueous) to give a dispersion of a larger particle size with an opaque or milky appearance. Slow addition of ammonia, at this point, helped to adjust particle size significantly lower to a translucent state with a dark amber tint with low viscosity. Then, 42.4 parts of styrene and 3.4 parts of di-vinyl benzene (DVB 80) was added and allowed to homogenize into the dispersion. To the resulting dispersion was free radical polymerized by adding 0.2 parts of a 1% Fe-EDTA and 2.4 parts of 3.5% t-butyl hydrogen peroxide which was allowed to mix into the dispersion prior to slowly adding 3.0 parts of 2.0% erythorbic acid at an initial temperature of 20° C. This resulted in a rather slow initiation and polymerization of the vinyl functional monomers, as evident by an exotherm from 20° C. to 34° C., at which point the viscosity increased requiring addition of 40 parts water. The vinyl polymerization was chased with a small amount of additional t-butyl hydrogen peroxide and erythorbic acid and applied heat to help complete the conversion of vinyl monomer to polymer. Afterwards, adipic dihydrazide was added to the dispersion providing a polymer with the potential to self-crosslink through a condensation of the hydrazide with ketones on the polymer; the effect of which was observed in a significant increase in hardness, and very good mar and black heel mark resistance for the dried coating. The final dispersion was low to moderate in particle size, low in sediment with a solids level of 39.6%, a viscosity of 73 cps (at 25° C.) at a pH of 7.5 with a particle size of 52.1 nm.

Example 11

Soy Oil Vinyl Copolymer Dispersion

A prepolymer was prepared by first homogenizing the polyol prepared in Example 2 (Item 1) with maleic anhydride by heating to 70° C. until the solid maleic anhydride is homogenized (melted) into the polyol. At this point the TEA and MMA (items 2 and 3) are added and the mixture held at 70° C. for 20 minutes. After which the mixture was allowed to cool to room temperature and allowed to continue to react over the next 45 minutes. This resulted in a prepolymer with a dark amber color of modest viscosity at room temperature (~22° C.) due to its dilution in MMA.

| Item # | Material | Parts |
|---|---|---|
| 1 | Reaction product from Example 2 | 58.3 |
| 2 | Maleic Anhydride | 6.0 |
| 3 | Methyl Methacrylate | 21.6 |
| 4 | Triethylamine | 1.6 |
| 5 | BHT | 0.1 |

The resulting prepolymer (85 parts) at about 21° C. was dispersed in water having an initial temperature of ~20° C. containing ammonia (3 parts 28% aqueous) to give a dispersion of a larger particle size with an opaque or milky appearance. Slow addition of ammonia at this point helped to adjust particle size significantly lower to a translucent state with a dark amber tint with low viscosity. Then, 21.9 parts of styrene and 2.6 parts of di-vinyl benzene (DVB 80) were added, followed by the addition of 42.5 parts water. These ingredients were then allowed to homogenize for approximately 45 minutes. The resulting dispersion was free radical polymerized by adding 0.2 parts of a 1% Fe-EDTA and 4.2 parts of 3.5% t-butyl hydrogen peroxide which was allowed to mix into the dispersion prior to slowly adding 5.3 parts of 2.0% erythorbic acid at an initial temperature of 20°

C. This resulted in a rather slow initiation and polymerization of the vinyl functional monomers with ~30% of total erythorbic acid added as evident by an exotherm from 19° C. to 23° C.; heat was applied to the dispersion to bring the temperature to 39° C. and the remaining erythorbic acid was slowly added over approximately 30 minutes. The vinyl polymerization was chased with a small amount of additional t-butyl hydrogen peroxide and erythorbic acid and applied heat to help complete the conversion of vinyl monomer to polymer. Afterwards, adipic dihydrazide was added to the dispersion providing a polymer with the potential to self-crosslink through a condensation of the hydrazide with ketones on the polymer; the effect of which was observed in a significant increase in hardness, and very good mar and black heel mark resistance for the dried coating. The final dispersion was low to moderate in particle size, low in sediment with a solids level of 34.6%, a viscosity of 33 cps (at 25° C.) at a pH of 8.1 with a particle size of 44.7 nm.

Example 12

Soy Oil Vinyl Copolymer Dispersion

A prepolymer was prepared by first homogenizing the polyol, prepared in Example 3 (Item 1), with maleic anhydride by heating to 70° C. until the solid maleic anhydride is homogenized (melted) into the polyol. At this point, the TEA and MMA (items 2 and 3) are added and the mixture held at 70° C. for 180 minutes. After which the mixture was allowed to cool to ~50° C. for dispersing into water. At this point most, if not all, of the anhydride has been consumed as evident in the FTIR spectrum not showing any significant peaks at 1779 and 1849 cm$^{-1}$. However, some anhydride peak might be buried under other absorption peaks, such as those for ester groups. This resulted in a prepolymer with a dark amber color of low viscosity at the dispersion temperature of about 50° C.

| Item # | Material | Parts |
|---|---|---|
| 1 | Reaction product from Example 3 | 64.0 |
| 2 | Maleic Anhydride | 6.0 |
| 3 | Methyl Methacrylate | 23.4 |
| 4 | Triethylamine | 2.5 |
| 5 | BHT | 0.1 |

The resulting prepolymer (91 parts of which) at about 50° C. was dispersed in 150 parts water, having an initial temperature of about 20° C., containing 0.7 parts potassium hydroxide and ammonia (0.9 parts 28% aqueous) to give a dispersion of a low particle size with a translucent appearance. Then, 38.7 parts of styrene, 2.8 parts butyl acrylate and 2.8 parts of hexane diol diacrylate was added and allowed to homogenize into the dispersion. The resulting dispersion was free radical polymerized by adding 0.03 parts of a 1% Fe-EDTA and 3.5 parts of 3.5% t-butyl hydrogen peroxide, which was allowed to mix into the dispersion prior to slowly adding 5.0 parts of 2.0% erythorbic acid, at an initial temperature of 20° C. This resulted in an initiation and polymerization of the vinyl functional monomers with an observed exotherm from 21° C. to 49° C. The vinyl polymerization was chased with a small amount of additional t-butyl hydrogen peroxide and erythorbic acid and applied heat to help complete the conversion of vinyl monomer to polymer. Afterwards, 5.0 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 43.1%, a viscosity of 185 cps (at 25° C.) at a pH of 7.1 with a particle size of 46.8 nm.

Example 13

Soy Oil Vinyl Copolymer Dispersion

A prepolymer was prepared by first homogenizing the polyol, prepared in Example 4 (Item 1), with maleic anhydride by heating to 70° C. until the solid maleic anhydride is homogenized (melted) into the polyol. At this point, the TEA and MMA (items 2 and 3) are added and the mixture held at 70° C. for 90 minutes. After which the mixture was allowed to cool to approximately 50° C. for dispersing into water. At this point most, if not all, of the anhydride has been consumed as evident in the FTIR spectrum not showing any significant peaks at 1779 and 1849 cm$^{-1}$. However, some anhydride peak might be buried under other absorption peaks such as those associated with ester groups. This resulted in a prepolymer with a dark amber color of low viscosity at the dispersion temperature of about 50° C.

| Item # | Material | Parts |
|---|---|---|
| 1 | Reaction product from Example 4 | 64.0 |
| 2 | Maleic Anhydride | 6.0 |
| 3 | Methyl Methacrylate | 23.4 |
| 4 | Triethylamine | 2.8 |
| 5 | BHT | 0.1 |

The resulting prepolymer (93.8 parts of which) at approximately 50° C. was dispersed in 150 parts water, having an initial temperature of about 20° C., containing 0.7 parts potassium hydroxide and ammonia (0.5 parts 28% aqueous) to give a dispersion of a low particle size with a translucent appearance. Then, 39.6 parts of styrene, 2.8 parts butyl acrylate and 2.0 parts of di-vinyl benzene (DVB 80) was added and allowed to homogenize into the dispersion; this resulted in a significant increase in particle size as evident by the dispersion having an opaque appearance. The resulting dispersion was free radical polymerized by adding 0.03 parts of a 1% Fe-EDTA and 3.5 parts of 3.5% t-butyl hydrogen peroxide which was allowed to mix into the dispersion prior to slowly adding 5.0 parts of 2.0% erythorbic acid at an initial temperature of 20° C. This resulted in an initiation and polymerization of the vinyl functional monomers with an observed exotherm from 20° C. to 36° C. The particle size was found to drop and the viscosity rise as the vinyl polymerization progressed. The vinyl polymerization was chased with a small amount of additional t-butyl hydrogen peroxide and erythorbic acid and applied heat to help complete the conversion of vinyl monomer to polymer. Afterwards 5.1 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 46.3%, a viscosity of 260 cps (at 25° C.) at a pH of 6.9 with a particle size of 63.3 nm.

Example 14

Soy Oil Vinyl Copolymer Dispersion

A prepolymer from the polyol, prepared in Example 5 (Item 1), was reacted with phthalic anhydride by mixing together in a reactor items 1-5 in the table below and heating to 70° C.-72° C. for 300 minutes. At this point, the prepolymer appeared to be homogeneous and all of the anhydride appears to have been reacted as evident in the FTIR spectrum not showing any significant anhydride peaks at 1779 and 1849 cm$^{-1}$. However, some anhydride peak might be buried under other absorption peaks such as those associated with ester groups. In any case, this resulted in a prepolymer with a dark amber color of relatively low viscosity at the dispersion temperature of approximately 50° C.

| Item # | Material | Parts |
| --- | --- | --- |
| 1 | Reaction product from Example 5 | 64.0 |
| 2 | Phthalic Anhydride | 10.4 |
| 3 | Methyl Methacrylate | 24.8 |
| 4 | Triethylamine | 2.7 |
| 5 | BHT | 0.1 |

The resulting prepolymer (93.8 parts of which) at ~50° C. was dispersed in 150 parts water having an initial temperature of ~20° C. containing 0.5 parts sodium hydroxide and 0.66 parts Dextrol OC-40 (neutralized with TEA) to give a dispersion of a moderate particle size after addition of a small amount of ammonia (~28% aqueous) to raise the pH to above 6.9. Then, 42.8 parts of styrene, 2.8 parts butyl acrylate and 2.8 parts of di-vinyl benzene (DVB 80) was added and allowed to homogenize into the dispersion which resulted in a significant increase in particle size as evident by the dispersion having an opaque appearance. The resulting dispersion was free radical polymerized by adding 0.1 parts of a 1% Fe-EDTA and 3.0 parts of 3.5% t-butyl hydrogen peroxide which was allowed to mix into the dispersion prior to slowly adding 4.0 parts of 2.0% erythorbic acid at an initial temperature of 35° C. This resulted in an initiation and slow polymerization of the vinyl functional monomers with an observed exotherm from 35° C. to 41° C. The dispersion thickened upon polymerization of the vinyl components; 19.1 parts of water was added to adjust viscosity. The vinyl polymerization was chased with a small amount of additional t-butyl hydrogen peroxide and erythorbic acid and applied heat to help complete the conversion of vinyl monomer to polymer. An additional 30.5 grams of water was added to reduce viscosity. Afterwards, 3.4 parts of adipic dihydrazide was added to the dispersion to provide a polymer with the potential to self-crosslink through a condensation of the hydrazide with ketones on the polymer. The final dispersion was low in sediment with a solids level of 42.5%, a viscosity of 440 cps (at 25° C.) at a pH of 7.5 with a particle size of 207.5 nm.

Example 15

Soy Oil Polyol Functionalized With Ketone/Acrylate

A poly(ketone/acrylate) functional oligomer was prepared by combining items 1-5 of the ingredients below in a 4 neck flask equipped with a thermometer, overhead stirrer and dry air inlet. With stirring and under a nitrogen blanket, the temperature of the reaction mixture was raised to 110° C. to 114° C. and held at this temperature for 1 hour. The temperature was then raised to 121° C.-125° C. and held at this temperature for 2 hours or until the acid number was <1.0 (mg KOH/g). The final material was clear with an amber tint and a viscosity of approximately 1,540 cps at 70° C. at an acid number of 0.7 mg KOH/g.

| Item # | Material | Parts |
| --- | --- | --- |
| 1 | Epoxidized Soybean Oil | 303.0 |
| 2 | Levulinic Acid | 33.6 |
| 3 | Methacrylic Acid | 24.9 |
| 4 | BHT | 0.2 |
| 5 | Zirconium Propionate (as a 20% solution in levulinic acid) | 2.0 |

Example 16

Soy Oil Vinyl Copolymer Dispersion

A prepolymer was prepared by first homogenizing the soy oil polyol prepared in Example 15 (Item 1), with succinic anhydride by heating to 120° C. until at least the solid succinic anhydride is homogenized (melted) into the polyol. The mixture was held at 120° C. for 2 hours at which point the FTIR of the material was checked and found to contain a large content of anhydride as evident by significant peaks at 1779 and 1849 cm$^{-1}$. It was accordingly deemed to be advisable to cool the reaction mixture as soon as the succinic anhydride was homogenized at 120° C. to a lower temperature (<90° C.) in order to add MMA as diluent and TEA as catalyst (and subsequent acid neutralizer/ionizer) to allow effective anhydride reaction with hydroxyls. The reaction mixture was accordingly cooled to 82° C.-84° C. and at this point the MMA and TEA (items 2 and 3) were added and the mixture was held at 82° C.-84° C. for 30 minutes. Most, if not all, of the anhydride had been consumed at this stage, as evident in the FTIR spectrum, not showing any significant peaks at 1779 and 1849 cm$^{-1}$. However, some anhydride peak might have been buried under other absorption peaks, such as those associated with ester groups. After that the mixture was allowed to cool to about 50° C. for dispersing into water. This resulted in a prepolymer with a lighter amber color and low viscosity at the dispersion temperature of about 50° C.

| Item # | Material | Parts |
| --- | --- | --- |
| 1 | Reaction product from Example 15 | 64.0 |
| 2 | Succinic Anhydride | 5.3 |
| 3 | Methyl Methacrylate | 23.1 |
| 4 | Triethylamine | 2.7 |
| 5 | BHT | 0.1 |

The resulting prepolymer (89.6 parts of which) at about 50° C. was dispersed in 150 parts water having an initial temperature of ~20° C. containing 1.5 g of 30% sodium lauryl sulphate to initially give a dispersion of large particle size. The addition of ammonia (~28% aqueous) reduced particle size significantly to eventually result in a low particle size at a pH of approximately 7.6. To the resulting dispersion, 19 parts of styrene, 2.8 parts butyl acrylate and 1.3 parts of di-vinyl benzene (DVB 80) was added and allowed to homogenize for at least 30 minutes into the dispersion. This resulted in a significant increase in particle size as evident by the dispersion having an opaque appearance. To the resulting dispersion was free radical polymerized by adding 0.2 parts of a 1% Fe-EDTA and 2.0 parts of 3.5% t-butyl hydrogen peroxide which was allowed to mix into the dispersion prior to slowly adding 2.8 parts of 2.0% erythorbic acid at an initial temperature of 19° C. This resulted in an initiation and slow polymerization of the vinyl functional monomers with an observed exotherm from 19° C. to 30° C. The particle size was observed to drop down upon polymerization of the vinyl components to become a translucent dispersion. The vinyl polymerization was chased with a small amount of additional t-butyl hydrogen peroxide and erythorbic acid. Afterwards, 2.9 parts of adipic dihydrazide was added to the dispersion to provide a polymer with the potential to self-crosslink through a condensation of the hydrazide with ketones on the polymer. The final dispersion was low in sediment with a solids level of 39.6%, a viscosity of 55 cps (at 25° C.) at a pH of 7.7 with a particle size of 68.0 nm.

Example 17

Soy Oil Vinyl Copolymer Dispersion

A prepolymer was prepared by first homogenizing the polyol, prepared in example 3 (Item 1), with maleic anhydride by heating to 70° C. until the solid maleic anhydride is homogenized (melted) into the polyol. At this point, the TEA and MMA (items 2 and 3) were added and the mixture was held at 70° C. for 180 minutes. After which, the mixture was allowed to cool to ~50° C. for dispersing into water. At that point most, if not all, of the anhydride had been consumed as evident in the FTIR spectrum not showing any significant peaks at 1779 and 1849 cm$^{-1}$. However, some anhydride peak might have been buried under other absorption peaks, such as those for ester groups. In any case, this resulted in a prepolymer with a dark amber color of low viscosity at the dispersion temperature of about 50° C.

| Item # | Material | Parts |
|---|---|---|
| 1 | Reaction product from example 3 | 64.0 |
| 2 | Maleic Anhydride | 6.0 |
| 3 | Methyl Methacrylate | 23.4 |
| 4 | Triethylamine | 2.2 |
| 5 | BHT | 0.1 |

Then, 93.5 parts of the resulting prepolymer at approximately 50° C. was dispersed in 150 parts water having an initial temperature of about 20° C. containing 0.7 parts potassium hydroxide and ammonia (0.9 parts 28% aqueous) to give a dispersion of a low particle size with a translucent appearance. After that 39.5 parts of styrene, 2.8 parts butyl acrylate and 1.8 parts of divinyl benzene was added and allowed to homogenize into the dispersion. Then the resulting dispersion was free radical polymerized by adding 0.03 parts of a 1% Fe-EDTA and 3.5 parts of 3.5% t-butyl hydrogen peroxide which was allowed to mix into the dispersion prior to slowly adding 5.0 parts of 2.0% erythorbic acid at an initial temperature of 20° C. This resulted in an initiation and polymerization of the vinyl functional monomers with an observed exotherm from 21° C. to 49° C. The vinyl polymerization was chased with a small amount of additional t-butyl hydrogen peroxide and erythorbic acid and applied heat to help complete the conversion of vinyl monomer to polymer. Afterwards, 5.0 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 43.5%, a viscosity of 53 cps (at 25° C.) at a pH of 7.2 with a particle size of 52.6 nm.

Example 18

Soy Oil Vinyl Copolymer Dispersion

A prepolymer was prepared by first homogenizing the polyol, prepared in example 3 (Item 1), with maleic anhydride by heating to 70° C. until the solid maleic anhydride is homogenized (melted) into the polyol. At this point, the TEA and MMA (items 2 and 3) were added and the mixture held at 70° C. for 180 minutes. After which, the mixture was allowed to cool to approximately 50° C. for dispersing into water. At this point most, if not all, of the anhydride had been consumed as evident in the FTIR spectrum not showing any significant peaks at 1779 and 1849 cm$^{-1}$. However, some anhydride peak might have been buried under other absorption peaks, such as those for ester groups. This resulted in a prepolymer with a dark amber color of low viscosity at the dispersion temperature of about 50° C.

| Item # | Material | Parts |
|---|---|---|
| 1 | Reaction product from example 3 | 64.0 |
| 2 | Maleic Anhydride | 6.0 |
| 3 | Methyl Methacrylate | 23.4 |
| 4 | Triethylamine | 2.2 |
| 5 | BHT | 0.1 |

Then, 93.2 parts of the resulting prepolymer at approximately 50° C. was dispersed in 150 parts water, having an initial temperature of about 20° C., containing 0.7 parts potassium hydroxide and ammonia (0.9 parts 28% aqueous), to give a dispersion of a low particle size with a translucent appearance. Then 32.5 parts of styrene, 2.9 parts butyl acrylate, 8.0 parts acrylonitrile and 2.1 parts of divinyl benzene was added and allowed to homogenize into the dispersion. The resulting dispersion was free radical polymerized by adding 0.03 parts of a 1% Fe-EDTA and 3.5 parts of 3.5% t-butyl hydrogen peroxide which was allowed to mix into the dispersion prior to slowly adding 5.0 parts of 2.0% erythorbic acid at an initial temperature of 20° C. This resulted in an initiation and polymerization of the vinyl functional monomers with an observed exotherm from 21° C. to 49° C. The vinyl polymerization was chased with a small amount of additional t-butyl hydrogen peroxide and erythorbic acid and applied heat to help complete the conversion of vinyl monomer to polymer. Afterwards, 5.1 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 44.7%, a viscosity of 95 cps (at 25° C.) at a pH of 6.8 with a particle size of 58.5 nm.

Example 19

Soy Oil Vinyl Copolymer Dispersion

A prepolymer was prepared by first homogenizing the polyol, prepared in example 3 (Item 1), with maleic anhydride by heating to 70° C. until the solid maleic anhydride is homogenized (melted) into the polyol. At this point, the TEA and MMA (items 2 and 3) are added and the mixture held at 70° C. for 180 minutes. After which the mixture was allowed to cool to approximately 50° C. for dispersing into water. At this point most, if not all, of the anhydride has been consumed as evident in the FTIR spectrum not showing any significant peaks at 1779 and 1849 $cm^{-1}$. However, some anhydride peak might be buried under other absorption peaks, such as those for ester groups. This resulted in a prepolymer with a dark amber color of low viscosity at the dispersion temperature of about 50° C.

| Item # | Material | Parts |
|--------|----------|-------|
| 1 | Reaction product from example 3 | 64.0 |
| 2 | Maleic Anhydride | 6.0 |
| 3 | Methyl Methacrylate | 23.4 |
| 4 | Triethylamine | 2.2 |
| 5 | BHT | 0.1 |

Then, 93.5 parts of the resulting prepolymer, at approximately 50° C., was dispersed in 150 parts water, having an initial temperature of about 20° C., containing 0.7 parts potassium hydroxide and ammonia (0.9 parts 28% aqueous) to give a dispersion of a low particle size with a translucent appearance. Then, 35.4 parts of styrene, 2.8 parts butyl acrylate and 6.3 parts of divinyl benzene was added and allowed to homogenize into the dispersion. To the resulting dispersion was free radical polymerized by adding 0.03 parts of a 1% Fe-EDTA and 3.5 parts of 3.5% t-butyl hydrogen peroxide which was allowed to mix into the dispersion prior to slowly adding 5.0 parts of 2.0% erythorbic acid at an initial temperature of 20° C. This resulted in an initiation and polymerization of the vinyl functional monomers with an observed exotherm from 21° C. to 49° C. The vinyl polymerization was chased with a small amount of additional t-butyl hydrogen peroxide and erythorbic acid and applied heat to help complete the conversion of vinyl monomer to polymer. Afterwards 5.1 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 40.6%, a viscosity of 81 cps (at 25° C.) at a pH of 7.0 with a particle size of 67.5 nm.

Coating Formulations

Coatings of the above dispersions where made on wood for testing of resistance properties and on steel panels for Konig Hardness testing. All coatings were used as is without any added co-solvent or coalescing agent and formed high quality glossy coatings with very little color development. All coatings where allowed to cure for 1 week, at room temperature, before testing. The hardness of the coatings is expressed in oscillation of the Koenig Hardness (pendulum hardness) testing apparatus. The water and 1% Spic and Span® spot tests where done by subjecting the coatings to the chemicals for 4 hours, removing the chemical and allowing a 1 hour recovery before evaluating. The 5% ammonia and 70% IPA spot tests where done by subjecting the coatings to the chemicals for 1 hour, removing the chemical and allowing a 1 hour recovery before evaluating. The area of exposure was then rated on a scale of 0 to 10 for its appearance; 0=removal of coating and 10=no effect on coating. Accordingly, the addition of suitable co-solvents can typically be utilized to improve resistance properties.

The results of the testing are shown in Table 1. The coatings show exceptional good hardness, alcohol resistance and black heel mark resistance (or mar resistance) without the addition of any added coalescent (i.e., organic solvent). The use of organic solvents as a coalescent in coatings contributes to VOC (volatile organic component) emissions. Many VOC's are dangerous to human health or cause harm to environment, such as contributing to the creation of smog. In the case of any reduced scores obtained in the spot tests was due to some degree of observed darkening of the wood substrate remaining after the test; however, this discoloration subsequently disappeared within several hours except for 5% ammonia. It would be anticipated that conventional formulation of the coatings of the invention should provide further improvement in coating properties. Typical waterborne acrylic or even polyurethanes would not be able to attain both the hardness and resistance properties shown by the invention examples without formulation with significant amounts of coalescing solvents.

TABLE 1

Soy-Styrene-Acrylate Copolymer Dispersion Coating Properties

| Polymer Evaluated | Water | 1% Spic N Span | 5% Ammonia | 70% IPA | Koenig Hardness (osc.) | Black Heel Mark | MFFT (° C.) |
|---|---|---|---|---|---|---|---|
| Example 8  | 10.0 | 7.0 | 7.0 | 9.5  | 78 | 8.5  | 9  |
| Example 9  | 10.0 | 7.0 | 8.0 | 9.5  | 82 | 8.0  | 12 |
| Example 10 | 10.0 | 8.0 | 8.0 | 9.5  | 68 | 8.0  | 8  |
| Example 11 | 10.0 | 8.0 | 7.0 | 9.5  | 59 | 9.0  | 5  |
| Example 13 | 9.0  | 9.0 | 7.0 | 9.5  | 52 | 9.0  | <5 |
| Example 17 | 9.0  | 9.5 | 7.0 | 10.0 | 26 | 9.5  | <5 |
| Example 18 | 8.0  | 9.0 | 8.0 | 9.5  | 24 | 10.0 | <5 |
| Example 19 | 8.0  | 9.0 | 8.0 | 9.5  | 29 | 8.5  | <5 |

Finally, the coatings of the invention provide useful properties while using significant quantities of renewable raw materials and provide for improved sustainability. The high amounts of renewable content, combined with the low VOC, are significant attributes of "green" products which are associated with having a reduced impact on the environment and human health. Furthermore, the overall raw material costs and processing requirements are quite low, particularly compared to the performance obtained, thus giving a high performance/cost ratio.

While residual hydroxyl groups are usually present on the prepolymer and downstream products thereof, it is anticipated that if residual hydroxyl groups were undesirable, the number of residual hydroxyl groups could be minimized or eliminated by urethane forming reactions with a monoisocyanate (e.g., phenylisocyanate) or ester forming reaction with a carboxylic acid containing species or anhydride thereof (e.g., acetic anhydride).

Example 20

Soy Oil-Vinyl Copolymer Dispersion

A prepolymer was prepared by first homogenizing a polyol as described in example 4 (Item 1) with maleic anhydride and MMA (items 1-3) by heating to 60-70 C until the solid maleic anhydride is homogenized (melted). The TEA (item 4) was then added and the mixture was held at 70° C. for 90 minutes. At this point most if not all of the anhydride had been consumed as evident in the FTIR spectrum not showing any significant peaks at 1779 and 1849 cm$^{-1}$. However, some anhydride peak might have been buried under other absorption peaks such as those for ester groups. After that the mixture was allowed to cool to 25-30° C., item 5 was added and homogenized into the prepolymer. This resulted in a prepolymer with a dark amber color of modest viscosity at the prepolymer dispersion temperature of ~25° C.

| Item # | Material | Parts |
|---|---|---|
| 1 | ESO-LA-MAA reaction product from example 4 | 64.0 |
| 2 | Maleic Anhydride | 4.7 |
| 3 | Methyl Methacrylate | 23.0 |
| 4 | Triethylamine | 2.4 |
| 5 | Ammonium Hydroxide (~29%) | 0.7 |

The resulting prepolymer (92.8 parts of which) at ~25° C. was dispersed in 150 parts water having an initial temperature of ~20° C. to give a dispersion of a low particle size with a translucent appearance. To the resulting dispersion 18.7 parts of styrene, 11.2 parts methyl methacrylate and 2.3 parts of di-vinyl benzene (DVB 80) was added and allowed to homogenize into the dispersion; this resulted in a increase in particle size as evident by the dispersion having an opaque appearance. The resulting dispersion was free radical polymerized by adding 0.03 parts of a 1% Fe-EDTA and 4.0 parts of 3.5% t-butyl hydrogen peroxide which was allowed to mix into the dispersion prior to slowly adding 5.0 parts of 2.0% erythorbic acid at an initial temperature of 20 C. This resulted in an initiation and polymerization of the vinyl functional monomers with an observed exotherm from 20° C. to 46° C. The particle size was found to drop and the viscosity rise as the vinyl polymerization progressed. The vinyl polymerization was chased with a small amount of additional t-butyl hydrogen peroxide and erythorbic acid and applied heat to help complete the conversion of vinyl monomer to polymer. Afterwards 3.9 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion was low in sediment with a solids level of 40.3%, a viscosity of 160 cps (at 25° C.) at a pH of 7.7 with a particle size of 47.3 nm.

Example 21

Soy Oil-Vinyl Copolymer Dispersion

A prepolymer and final dispersion was prepared in a similar manner as described in Example 20 with the exception that after completing the vinyl polymerization, 2% of sodium bisulfite versus solids was added slowly as a 25% aqueous solution neutralized with ammonia to bring the pH>7.0. The final dispersion was low in sediment with a solids level of 38.7%, a viscosity of 78 cps (at 25° C.) at a pH of 8.5 with a particle size of 44.9 nm. The significant difference between this dispersion and that obtained in example 20 is in long term and hot storage stability. The present example passed storage at 60° C. for 1 week and 52° C. for 1 month, whereas example 20 did not pass and showed complete gelation after less than one day at 60° C.

Example 22

Soy Oil-Vinyl Copolymer Dispersion

A prepolymer was prepared by first homogenizing a polyol as described in example 4 (Item 1) with maleic anhydride and MMA (items 1-3) by heating to 60-70° C. until the solid maleic anhydride is homogenized (melted). The TEA (item 4) was then added and the mixture held at 70° C. for 90 minutes. At this point, most if not all of the anhydride has been consumed as evident in the FTIR spectrum not showing any significant peaks at 1779 and 1849 cm$^{-1}$. However, some anhydride peak might have been buried under other absorption peaks, such as those for ester groups. In any case, after which the mixture was allowed to cool to 25-30° C. and item 5 was added and homogenized into the prepolymer. This resulted in a prepolymer with a dark amber color of modest viscosity at the prepolymer dispersion temperature of ~25° C.

| Item # | Material | Parts |
|---|---|---|
| 1 | ESO-LA-MAA reaction product from example 4 | 250.6 |
| 2 | Maleic Anhydride | 14.9 |
| 3 | Methyl Methacrylate | 88.6 |
| 4 | Triethylamine | 7.7 |
| 5 | Ammonium Hydroxide (~29%) | 1.8 |

The resulting prepolymer (180 parts of which) at ~25° C. was dispersed in 297 parts water having an initial temperature of ~20° C. to give a dispersion of a low particle size with a translucent appearance. To the resulting dispersion 37.0 parts of styrene, 22.2 parts methyl methacrylate and 4.6 parts of di-vinyl benzene (DVB 80) was added and allowed to homogenize into the dispersion; this resulted in a increase in particle size as evident by the dispersion having an opaque appearance. To the resulting dispersion was free radical polymerized by adding 0.03 parts of a 1% Fe-EDTA and 8.0 parts of 3.5% t-butyl hydrogen peroxide which was allowed to mix into the dispersion prior to slowly adding 10.0 parts of 2.0% erythorbic acid at an initial temperature of 20° C. This resulted in an initiation and polymerization of the vinyl functional monomers with an observed exotherm from 20° C. to 41° C. The particle size was found to drop and the viscosity rise as the vinyl polymerization progressed. The vinyl polymerization was chased with a small amount of additional t-butyl hydrogen peroxide and erythorbic acid and applied heat to help complete the conversion of vinyl monomer to polymer. Afterwards 7.7 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion had a sediment level of 0.3%, with a solids level of 43.0%, a viscosity of 180 cps (at 25° C.) at a pH of 6.7 with a particle size of 82.0 nm. Hot storage stability was poor with the gel occurring after only one day at 60° C.

Example 23

Soy Oil-Vinyl Copolymer Dispersion

A prepolymer, similar to Example 22 above, was prepared by first homogenizing a polyol (Item 1), prepared as described in example 4, with maleic anhydride and MMA (items 2 and 3) by heating to 60-70° C. until the solid maleic anhydride is homogenized (melted). The TEA (item 4) was then added and the mixture held at 70° C. for 90 minutes. At this point most if not all of the anhydride has been consumed as evident in the FTIR spectrum not showing any significant peaks at 1779 and 1849 cm$^{-1}$. However, some anhydride peak might have been buried under other absorption peaks, such as those for ester groups. After which a sodium sulfite solution in water (item 5) was added to the prepolymer and homogenized resulting in an opaque mixture. This was held at 50° C. for 1 hour. This resulted in a prepolymer that was clear (no longer opaque) with a dark amber color and low viscosity at a temperature of ~50 C.

| Item # | Material | Parts |
|---|---|---|
| 1 | ESO-LA-MAA reaction product from example 4 | 250.6 |
| 2 | Maleic Anhydride | 14.9 |
| 3 | Methyl Methacrylate | 88.6 |
| 4 | Triethylamine | 7.7 |
| 5 | 25% Aqueous Sodium Sulfite | 39.8 |

The resulting prepolymer (180 parts of which) at ~50° C. was dispersed in 297 parts water having an initial temperature of ~20° C. to give a dispersion of a low particle size with a translucent appearance. To the resulting dispersion 37.0 parts of styrene, 22.2 parts methyl methacrylate and 4.6 parts of di-vinyl benzene (DVB 80) was added and allowed to homogenize into the dispersion; this resulted in a increase in particle size as evident by the dispersion having an opaque appearance. To the resulting dispersion was free radical polymerized by adding 0.03 parts of a 1% Fe-EDTA and 8.0 parts of 3.5% t-butyl hydrogen peroxide which was allowed to mix into the dispersion prior to slowly adding 10.0 parts of 2.0% erythorbic acid at an initial temperature of 20° C. This resulted in an initiation and polymerization of the vinyl functional monomers with an observed exotherm from 20° C. to 44° C. The particle size was found to drop and the viscosity rise as the vinyl polymerization progressed. The vinyl polymerization was chased with a small amount of additional t-butyl hydrogen peroxide and erythorbic acid and applied heat to help complete the conversion of vinyl monomer to polymer. Afterwards 7.7 parts of adipic dihydrazide was added to the dispersion to provide a polymer with the potential to self-crosslink through a condensation of the hydrazide with ketones on the polymer; the effect of which was observed in a significant increase in hardness, and very good mar and black heel mark resistance for the dried coating. The final dispersion had a negligible sediment level of <0.1%, with a solids level of 43.3%, a viscosity of 64 cps (at 25° C.) at a pH of 6.9 with a particle size of 57.0 nm. Hot storage stability was excellent as dispersion shows little change in viscosity or PS after in 1 week at 60° C. By comparison to example 22, the addition of sulfite (or bisulfite) to the prepolymer prior to dispersing into water provided for improved dispersion quality as well as hot storage stability.

Example 24

Soy Oil-Vinyl Copolymer Polyurethane Composite

A prepolymer was prepared by first homogenizing a polyol as described in example 4 (Item 1) with maleic anhydride and MMA (items 1-3) by heating to 60-70° C. until the solid maleic anhydride was homogenized (melted). The TEA (item 4) was then added and the mixture was held at 70° C. for 120 minutes. At this point most, if not all, of the anhydride had been consumed as evident in the FTIR spectrum not showing any significant anhydride peaks at 1779 and 1849 cm$^{-1}$. However, some anhydride peak might have been buried under other larger absorption peaks, such as those for ester groups. After which the mixture was allowed to cool to 25-30° C. and item 5 is added and homogenized into the composition. This resulted in a prepolymer with a dark amber color of modest viscosity at the prepolymer dispersion temperature of about 25° C.

| Item # | Material | Parts |
|---|---|---|
| 1 | ESO-LA-MAA reaction product from example 4 | 64.0 |
| 2 | Maleic Anhydride | 3.8 |
| 3 | Methyl Methacrylate | 22.6 |
| 4 | Triethylamine | 1.9 |
| 5 | Ammonium Hydroxide (~29%) | 0.9 |

The resulting prepolymer (90 parts of which) at ~25 C was dispersed in 139 parts water and 292.4 parts of Sancure 970 (a relatively hard polyurethane dispersion of 42% solids) having an initial temperature of ~20° C. This produced a dispersion of a moderate particle size with a somewhat hazy appearance to it. To the resulting dispersion 17.5 parts of styrene, 13.5 parts methyl methacrylate and 2.2 parts of di-vinyl benzene (DVB 80) was added and allowed to homogenize into the dispersion; this resulted in a increase in particle size as evident by the dispersion having an opaque appearance. The resulting dispersion was free radical polymerized by adding 0.03 parts of a 1% Fe-EDTA and 4.0 parts of 3.5% t-butyl hydrogen peroxide which was allowed to mix into the dispersion prior to slowly adding 5.0 parts of 2.0% erythorbic acid at an initial temperature of 20° C. This resulted in an initiation and polymerization of the vinyl functional monomers with an observed exotherm from 20° C. to 46° C. The particle size was found to drop as the vinyl polymerization progressed. The vinyl polymerization was chased with a small amount of additional t-butyl hydrogen peroxide and erythorbic acid and applied heat to help complete the conversion of vinyl monomer to polymer. Afterwards 30.5 parts of water and 3.7 parts of adipic dihydrazide was added to the dispersion to provide a polymer with the potential to self-crosslink through a condensation of the dihydrazide with ketone functionality on the polymer. The final dispersion was low in sediment with a solids level of 41.4%, a viscosity of 230 cps (at 25° C.) at a pH of 7.6 with a particle size of 76.1 nm.

Example 25

Soy Based Prepolymer for Soy Oil-Vinyl Copolymer Polyurethane Composite (or Hybrid) Dispersion A prepolymer was prepared by first homogenizing a polyol as described in example 4 (Item 1) with maleic anhydride and MMA (items 1-3) by heating to 60-70° C. until the solid maleic anhydride is homogenized (melted). The TEA (item 4) was then added and the mixture was held at 70° C. for 120 minutes. At this point most if not all of the anhydride had been consumed as evident in the FTIR spectrum not showing any significant anhydride peaks at 1779 and 1849 cm$^{-1}$. However, it is possible that some anhydride peak might have been buried under other larger absorption peaks, such as those for ester groups. In any case, this resulted in a prepolymer with a dark amber color of modest viscosity at the prepolymer dispersion temperature of about 25° C. 200 g of the resulting prepolymer was dispersed into 540 grams of water and subsequently used in the preparation of the dispersion described in example 26.

| Item # | Material | Parts |
|---|---|---|
| 1 | ESO-LA-MAA reaction product from example 4 | 264.0 |
| 2 | Maleic Anhydride | 27.4 |
| 3 | Methyl Methacrylate | 97.2 |
| 4 | Triethylamine | 14.1 |

Example 26

Soy Oil-Vinyl Copolymer Polyurethane Composite (or Hybrid) Dispersion

A prepolymer was prepared by combining items 1-3 of the ingredients below at a temperature of 60° C. to a 4 neck flask equipped with a thermometer, overhead stirrer and gas inlet. The reaction below was run under a stream of dry nitrogen introduced through the gas inlet on the reactor. The temperature of the reaction mixture was raised to 102° C. to 105° C. and held at this temperature for 120 minutes or until theoretical NCO was reached as indicated by titration of a small sample. Item 4 was then added and the temperature adjusted to at 72° C. to 75° C. at which point item 5 was then added. The temperature was then adjusted to 84-87° C. and held there for 1 hour or until the theoretical NCO % was reached as indicated by titration of a small sample. When the prepolymer reached the theoretical NCO, the prepolymer temperature was dropped to 57-60° C. and item 6 was added and homogenized into the prepolymer. Afterwards, item 8 was added and homogenized into the prepolymer at 57-60° C. to neutralize (ionize) the prepolymer which is then dispersed shortly afterwards.

| Item # | Material | Parts by wt. |
|---|---|---|
| 1 | Piothane 67-500 HNA (OH# = 223.2) | 165.3 |
| 2 | Trimethylol Propane | 3.7 |
| 3 | Di-cyclohexylmethane Di-isocyanate | 254.5 |
| 4 | Methyl Methacrylate | 112.6 |
| 5 | Dimethylolpropionic Acid | 21.5 |
| 6 | Triethylamine | 20.2 |

A 208.2 g portion of the resulting neutralized prepolymer was dispersed into 540 g of water containing 200 g of the soy based prepolymer described in Example 25 that was adjusted to a pH of 7.1 with triethylamine. The temperature of the water containing the dispersed soy prepolymer was initially about 20-22° C. and maintained at a water/dispersion temperature below 28° C. while the polyurethane prepolymer described above was dispersed into it. The dispersed prepolymer was extended with 16.2 parts hydrazine hydrate (35% hydrazine content). After allowing 5 minutes after hydrazine addition, 5.7 parts of a 25% aqueous solution of ethylenediamine was added to complete the chain extension; this resulted in a significant rise in the dispersed particle size. After allowing about 30 minutes for chain extension the temperature of the dispersion was adjusted to 33-35° C. and 0.1 parts of a 1% solution Fe-EDTA complex, 8.0 parts of aqueous 3.5% tert-butyl hydrogen peroxide, and 12.0 parts of 2.0% aqueous erythorbic acid neutralized with triethylamine. The resulting exotherm indicated initiation and polymerization of the acrylic monomer present. To this dispersion adipic dihydrazide (ADH) was added to allow self-crosslinking between carbonyl/ketone groups incorporated into the polyurethane polymer phase via the carbonyl/ketone functional diol reaction with a diisocyanate. This resulted in a 38.2% solids polyurethane-soy-vinyl copolymer dispersion with low sediment having a viscosity of 98 cps (at 25° C.) at a pH of 7.2 with a particle size of 156.2 nm. The polyurethane-soy-vinyl copolymer dispersion produces a hard, tough, resistant coating at room temperature (about 21° C.) without the addition of added coalescent.

The same polyurethane prepolymer dispersed, chain extended and free radically polymerized under similar conditions without the soy prepolymer in the aqueous phase produced a 38.2% solids polyurethane-acrylic dispersion with low sediment having a viscosity of 918 cps (at 25° C.) at a pH of 8.3 with a particle size of 53.0 nm. The resulting polyurethane-acrylic dispersion does not produce a coalesced coating without the addition of coalescing solvents (>275 g/L coalescing solvent required for film formation).

While certain representative embodiments and details have been shown for the purpose of illustrating the subject invention, it will be apparent, to those skilled in this art, that various changes and modifications can be made therein without departing from the scope of the subject invention.

What is claimed is:

1. A self-crosslinkable prepolymer composition which is comprised of at least one triglyceride oil having appended thereto (1) hydroxyl groups, (2) moieties, which contain at least one aldehyde group or at least one ketone group, and (3) moieties, which contain at least one vinyl and/or substituted vinyl group.

2. The self-crosslinkable prepolymer composition, as specified in claim 1, wherein the triglyceride oil has epoxy groups appended thereto.

3. The self-crosslinkable prepolymer composition, as specified in claim 1, further comprising a moiety containing at least one free carboxylic acid group or an ionized carboxylic acid group appended to said at least one triglyceride oil.

4. The self-crosslinkable prepolymer, as specified in claim 1, wherein the moieties, which contain at least one aldehyde group or at least one ketone group are of the formula:

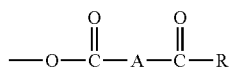

wherein A represents a hydrocarbyl moiety, containing from 1 to 20 carbon atoms and wherein R represents a hydrogen atom or an alkyl group containing from 1 to 8 carbon atoms.

5. The self-crosslinkable prepolymer, as specified in claim 1, wherein the moieties, which contain at least one aldehyde group or at least one ketone group are of the formula:

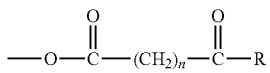

wherein n represents an integer from 1 to 8 and wherein R represents a hydrogen atom or a methyl group.

6. The self-crosslinkable prepolymer, as specified in claim 5, wherein n represents 2 and R represents a methyl group.

7. The self-crosslinkable prepolymer, as specified in claim 1, wherein the moieties, which contain at least one vinyl and/or substituted vinyl group are of a formula selected from the group consisting of:

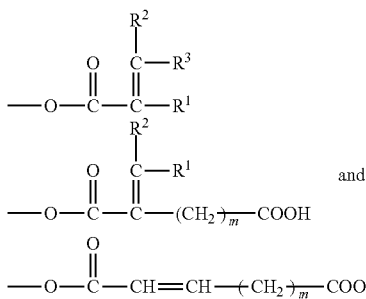
and or are a mixture of such moieties, wherein m represents an integer from 0 to 8, and wherein $R^1$, $R^2$, and $R^3$ can be the same or different and represents hydrogen atoms or alkyl groups containing from 1 to 8 carbon atoms and wherein said self-crosslinkable prepolymer is water dispersible.

8. The self-crosslinkable prepolymer, as specified in claim 7, wherein m represents 0.

9. The self-crosslinkable prepolymer composition, as specified in claim 1, wherein the prepolymer is copolymerized with a monomer(s) selected from
  (i) alkyl acrylates of the formula:

wherein $R^7$ is an alkyl group containing 1 to 15 carbon atoms, an alkoxyalkyl group containing a total of 1 to 10 carbon atoms, a cyanoalkyl group containing 1 to 10 carbon atoms, or a hydroxy alkyl group containing from 1 to 18 carbon atoms;
  (ii) alkyl alkacrylates of the formula:

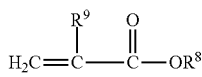

wherein $R^8$ is an alkyl group containing 1 to 15 carbon atoms, an alkoxyalkyl group containing a total of 1 to 10 carbon atoms, a cyanoalkyl group containing 1 to 10 carbon atoms, or a hydroxy alkyl group containing from 1 to 18 carbon atoms and wherein $R^9$ is an alkyl containing from 1 to 4 carbon atoms;
  (iii) unsaturated acids selected from acrylic acid, methacrylic acid, itaconic acid, maleic acid, fumaric acid, 2-carboxyethyl acrylate, mono methyl maleate, mono methyl fumarate, and mono methyl itaconate;
  (iv) vinyl substituted aromatic compounds selected from styrene, alkyl substituted styrene 1-vinylnaphthalene, 2-vinylnaphthalene, 3-methyl styrene, vinyltoluene, alpha-methylstyrene, 4-n-propyl styrene, 4-t-butyl styrene, 4-dodecyl-styrene, 4-cyclohexylstyrene, 2-ethyl-4-benzylstyrene, 4-methoxy-styrene, 4-dimethylaminostyrene, 3,5-diphenoxystyrene, 4-p-tolyl styrene, 4-phenyl styrene, 4,5-dimethyl-1-vinylnaphthalene, and 3-n-propyl-2-vinyl-naphthalene;
  (v) vinyl chloride;
  (vi) vinylidene chloride;
  (vii) butadiene;
  (viii) vinyl esters of the formula:

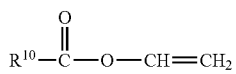

wherein $R^{10}$ is an alkyl group generally having from 1 to 10 or 12 carbon atoms;
  (ix) vinyl ethers of the formula:

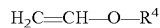

wherein $R^4$ is desirably an alkyl having from 1 to 10 carbon atoms;
  (x) acrylamide monomers of the formula:

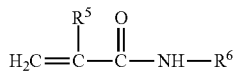

wherein $R^5$ represents a hydrogen atom or a methyl group and wherein $R^6$ is represents a hydrogen atom or an alkyl group (straight chained or branched) containing from 1 to 18 carbon atoms;
  (xi) functionalized acrylamides selected from 2-acrylamido-2-methylpropanesulfonic acid, and dimethylaminopropyl methacrylamide; and
  (xii) acrylonitriles selected from acrylonitrile, methacrylonitrile, and ethacrylonitrile.

10. An aqueous dispersion formed by dispersing the prepolymer described in claim 1 into another waterborne polymer.

* * * * *